United States Patent
Taniguchi et al.

(10) Patent No.: US 8,681,328 B2
(45) Date of Patent: Mar. 25, 2014

(54) DARK-FIELD DEFECT INSPECTING METHOD, DARK-FIELD DEFECT INSPECTING APPARATUS, ABERRATION ANALYZING METHOD, AND ABERRATION ANALYZING APPARATUS

(75) Inventors: Atsushi Taniguchi, Fujisawa (JP); Taketo Ueno, Kawasaki (JP); Yukihiro Shibata, Fujisawa (JP); Shunji Maeda, Yokohama (JP); Tetsuya Matsui, Hitachi (JP)

(73) Assignee: Hitachi High-Technologies Corporation, Tokyo (JP)

( * ) Notice: Subject to any disclaimer, the term of this patent is extended or adjusted under 35 U.S.C. 154(b) by 162 days.

(21) Appl. No.: 13/142,328

(22) PCT Filed: Jan. 20, 2010

(86) PCT No.: PCT/JP2010/050642
§ 371 (c)(1),
(2), (4) Date: Aug. 12, 2011

(87) PCT Pub. No.: WO2010/084884
PCT Pub. Date: Jul. 29, 2010

(65) Prior Publication Data
US 2011/0286001 A1   Nov. 24, 2011

(30) Foreign Application Priority Data

Jan. 26, 2009  (JP) .................... 2009-014299
Nov. 13, 2009  (JP) .................... 2009-259488

(51) Int. Cl.
*G01N 21/00*  (2006.01)
(52) U.S. Cl.
USPC ...................................... 356/237.2
(58) Field of Classification Search
USPC ...................................... 356/237.2
See application file for complete search history.

(56) References Cited

U.S. PATENT DOCUMENTS 6,628,381 B1 * 9/2003 Komem et al. ............ 356/237.4
2010/0214561 A1  8/2010 Chikamatsu et al.

FOREIGN PATENT DOCUMENTS

| JP | 07-139930 | 6/1995 |
| JP | 08-122262 | 5/1996 |
| JP | 2007-248086 | 9/2007 |
| JP | 2007-273513 | 10/2007 |

* cited by examiner

*Primary Examiner* — Roy M Punnoose
(74) *Attorney, Agent, or Firm* — Antonelli, Terry, Stout & Kraus, LLP.

(57) ABSTRACT

By including an illumination system and a detection system, an information collecting function of monitoring an environment, such as temperature and atmospheric pressure, and an apparatus state managing function having a feedback function of comparing the monitoring result and a design value, a theoretical calculation value or an ideal value derived from simulation results and calibrating an apparatus so that the monitoring result is brought close to the ideal value, a unit for keeping the apparatus state and apparatus sensitivity constant is provided. A control unit 800 is configured to include a recording unit 801, a comparing unit 802, a sensitivity predicting unit 803, and a feedback control unit 804. In the comparing unit 802, the monitoring result transmitted from the recording unit 801 and an ideal value stored in a database 805 are compared with each other. When a difference between the ideal value and the monitoring result exceeds a predetermined threshold, the feedback control unit 804 corrects the illumination system and the detection system.

18 Claims, 20 Drawing Sheets

DARK-FIELD DEFECT INSPECTING METHOD, DARK-FIELD DEFECT INSPECTING APPARATUS, ABERRATION ANALYZING METHOD, AND ABERRATION ANALYZING APPARATUS

TECHNICAL FIELD

The present invention relates to an apparatus having a function of monitoring an apparatus state of a dark-field defect inspecting apparatus for use in semiconductor manufacturing and magnetic head manufacturing lines, a function of calibrating an apparatus state based on monitoring results, in particular, a function of calibrating an apparatus state based on the monitoring results, and a function of predicting an anomaly state, and a predicting method of the apparatus.

BACKGROUND ART

A dark-field defect inspecting apparatus is an inspecting apparatus with the aim of observing a high-contrast ultrafine structure and performing a defect inspection by observing scattered light from an observation test sample.

In the semiconductor manufacturing apparatus, efforts have been underway in order to stabilize an apparatus called EES (Equipment Engineering System), reduce a difference in performance among apparatuses, and predict sporadic failure. In EES, it has been sought to achieve the above-mentioned aim by collecting, storing, and processing a large amount of data of a whole process.

In semiconductor manufacturing and magnetic head manufacturing lines, with microfabrication of an inspection subject, a defect signal to be detected becomes weaker. In particular, in a dark-field defect inspecting apparatus, scattered light is used for defect detection, and demands for stably detecting weak light are strong. To stably detect weak light, the apparatus state is desired to be kept constant at a high level.

Japanese Patent Application Laid-Open Publication No. 2007-273513 (Patent Document 1) discloses an automatic calibration technology for a spatial filter mounted in a dark-field inspecting apparatus. In this technology, diffracted light from a periodic pattern on a subject wafer is observed on a pupil, and the spatial filter is automatically set so that the transmission light amount is minimum.

Japanese Patent Application Laid-Open Publication No. 2007-248086 (Patent Document 2) describes an apparatus including a mechanism correcting a change in imaging position of an imaging lens due to changes in temperature and atmospheric pressure in an inspecting apparatus.

PRIOR ART DOCUMENTS

Patent Documents

Patent Document 1: Japanese Patent Application Laid-Open Publication No. 2007-273513
Patent Document 2: Japanese Patent Application Laid-Open Publication No. 2007-248086

DISCLOSURE OF THE INVENTION

Problems to be Solved by the Invention

However, even in the semiconductor inspecting apparatus of each of the documents mentioned above, management is not directed to the entire apparatus, but only a part of functions is managed and corrected. It is often the case that a plurality of inspecting apparatuses are arranged in a manufacturing line, and matching in detection sensitivity among the apparatuses is an important issue. Furthermore, for stable operation of the manufacturing line, defect prediction in the inspecting apparatus is also desired.

A preferred aim of the present invention to provide means for keeping the apparatus state and apparatus sensitivity constant by including an illumination optical system and a detection system, an information collecting function of monitoring an environment, such as temperature and atmospheric pressure, and an apparatus state managing function having a feedback function of comparing the monitoring result and a design value, a theoretical calculation value or an ideal value derived from simulation results and calibrating an apparatus so that the monitoring result is brought close to the ideal value.

The above and other preferred aims and novel characteristics of the present invention will be apparent from the description of the present specification and the accompanying drawings.

Means for Solving the Problems

The typical ones of the inventions disclosed in the present application will be briefly described as follows.

A dark-field defect inspecting method related to a typical embodiment of the present invention has a feature of obtaining, by a first sensor of a detection system, a signal of scattered light occurring due to illumination light illuminating a surface of an inspection subject, from the surface of the inspection subject and detecting a foreign substance or a defect on the inspection subject based on the signal obtained by the first sensor, the method including: an illumination light monitoring step of measuring either one or both of an intensity distribution and a polarization state distribution of the illumination light; a detection system monitoring step of detecting an imaging characteristic of a detection lens and a state of operation of a stage on which the inspection subject is placed, by detecting light input to the detection system by a second sensor; and a feedback control step of comparing detection results in the illumination light monitoring step and the detection system monitoring step and ideal values and adjusting either one or both of the illumination light and the detection system so that differences between the detection results and the ideal values are each equal to or smaller than an allowable value.

In the dark-field defect inspecting method, the illumination light monitoring step measures either one or both of the intensity distribution and the polarization state distribution of the illumination light by using a specular reflected light.

In the dark-field defect inspecting method, the illumination light monitoring step measures either one or both of the intensity distribution and the polarization state distribution of the illumination light on the stage serving as an inspection surface for the inspection subject.

In the dark-field defect inspecting method, the illumination light is generated by an illumination system having a laser as a light source, and, in the illumination light monitoring step, from measurement results of light beams in a process of generating the illumination light, either one or both of the intensity distribution and the polarization state distribution of the illumination light on an inspection surface are estimated.

In the dark-field defect inspecting method, the detection system monitoring step detects, by the second sensor, the scattered light obtained by obliquely illuminating a reflective-type optical element with spot light, the optical element having a known characteristic and being placed on the stage serving as an inspection surface for the inspection subject.

The dark-field defect inspecting method further includes an apparatus anomaly checking step of recording changes with time of the detection results in the illumination light monitoring step and the detection system monitoring step and determining an anomaly of an apparatus configuration through a statistical process.

The dark-field defect inspecting method further includes a detection result output step of simultaneously displaying the detection results in the illumination light monitoring step and the detection system monitoring step and the ideal values.

Another dark-field defect inspecting method related to the typical embodiment of the present invention has a feature of obtaining, by a first sensor of a detection system, a signal of scattered light occurring due to illumination light illuminating a surface of an inspection subject, from the surface of the inspection subject and detecting a foreign substance or a defect on the inspection subject based on the signal obtained by the first sensor, the method including: an illumination light monitoring step of measuring either one or both of an intensity distribution and a polarization state distribution of the illumination light; a detection system monitoring step of detecting an imaging characteristic of a detection lens and a state of operation of a stage on which the inspection subject is placed, by the scattered light input to the detection system by a second sensor; an environment measuring step of measuring either one or both of temperature and an atmospheric pressure upon execution of the illumination light monitoring step and the detection system monitoring step; and a feedback control step of comparing detection results in the illumination light monitoring step, the detection system monitoring step, and the environment measuring step and ideal values and adjusting either one or both of the illumination light and the detection system so that differences between the detection results and the ideal values are each equal to or smaller than an allowable value.

The dark-field defect inspecting method further includes a detection result output step of displaying the detection results in the illumination light monitoring step and the detection system monitoring step and the ideal values.

A dark-field defect inspecting apparatus related to a typical embodiment of the present invention includes: an illumination system outputting illumination light; a detection system detecting scattered light of the illumination light with which an inspection subject is illuminated; and a control unit, the apparatus obtaining, by a first sensor of the detection system, a signal of the scattered light occurring due to the illumination light illuminating a surface of the inspection subject, from the surface of the inspection subject and detecting a foreign substance or a defect on the inspection subject based on the obtained signal, the illumination system including illumination light monitoring unit for measuring either one or both of an intensity distribution and a polarization state distribution of the illumination light, the detection system including detection system monitoring unit for detecting an imaging characteristic of a detection lens and a state of operation of a stage on which the inspection subject is placed, by detecting light input to the detection system by a second sensor, and the control unit comparing detection results of the illumination light monitoring unit and the detection system monitoring unit and ideal values and adjusting either one or both of the illumination light and the detection system so that differences between the detection results and the ideal values are each equal to or smaller than an allowable value.

In the dark-field defect inspecting apparatus, the illumination light monitoring unit measures either one or both of the intensity distribution and the polarization state distribution of the illumination light by using specular reflection light.

In the dark-field defect inspecting apparatus, the illumination light monitoring unit measures either one or both of the intensity distribution and the polarization state distribution of the illumination light on the stage serving as an inspection surface for the inspection subject.

In the dark-field defect inspecting apparatus, a light source of the illumination light is a laser inside the illumination system, and the illumination light monitoring unit estimates, from measurement results of light beams in a process of generating the illumination light, either one or both of the intensity distribution and the polarization state distribution of the illumination light on an inspection surface.

In the dark-field defect inspecting apparatus, the detection system monitoring unit detects, by the second sensor, the scattered light obtained by obliquely illuminating a reflective-type optical element with spot light, the optical element having a known characteristic and being placed on the stage serving as an inspection surface for the inspection subject.

In the dark-field defect inspecting apparatus, the detection system monitoring unit detects, by the second sensor, predetermined light obtained by using a point source of light placed on the stage serving as an inspection surface for the inspection subject and a transmission-type optical element having a known characteristic.

The dark-field defect inspecting apparatus further includes apparatus anomaly checking unit for recording changes with time of the detection results of the illumination light monitoring unit and the detection system monitoring unit and determining an anomaly of an apparatus through a statistical process.

The dark-field defect inspecting apparatus further includes detection result output unit for simultaneously displaying the detection results of the illumination light monitoring unit and the detection system monitoring unit and the ideal values.

Another dark-field defect inspecting apparatus related to a typical embodiment of the present invention includes: an illumination system outputting illumination light; a detection system detecting scattered light of the illumination light with which an inspection subject is illuminated; and a control unit, the apparatus obtaining, by a first sensor of the detection system, a signal of the scattered light occurring, due to the illumination light illuminating a surface of the inspection subject, from the surface of the inspection subject and detecting a foreign substance or a defect on the inspection subject based on the obtained signal, the illumination system including an illumination light monitoring unit for measuring either one or both of an intensity distribution and a polarization state distribution of the illumination light, the detection system including a detection system monitoring unit for detecting an imaging characteristic of a focus detection lens and a state of operation of a stage on which the inspection subject is placed, by detecting the light input to the detection system by a second sensor, and the control unit including a comparing unit comparing detection results of the illumination light monitoring unit and the detection system monitoring unit and ideal values; an environment measuring unit for measuring either one or both of temperature and an atmospheric pressure upon executing the illumination light monitoring unit and the detection system monitoring unit; and a feedback unit for comparing detection results of the illumination light monitoring unit, the detection system monitoring unit, and the environment measuring unit and the ideal values calculated in advance and adjusting either one or both of the illumination light and the detection system so that differences between the detection results and the ideal values are each equal to or smaller than an allowable value.

The dark-field defect inspecting apparatus further includes a detection result output unit for displaying the detection results of the illumination light monitoring unit, the detection system monitoring unit, and the environment measuring unit and the respective ideal values.

Effects of the Invention

The effects obtained by typical aspects of the present invention will be briefly described below.

According to the calibrating method of the dark-field defect inspecting apparatus related to a typical embodiment of the present invention, apparatus performance of the dark-field defect inspecting apparatus is stabilized. Also, by using the same specifications of adjustment among apparatuses, a difference in sensitivity between apparatuses is reduced. Furthermore, by detecting a sign of an apparatus defect, an operating rate of the apparatus is improved.

BRIEF DESCRIPTIONS OF THE DRAWINGS

DESCRIPTIONS OF THE PREFERRED EMBODIMENTS (Existing Aspect)

Figure 1:
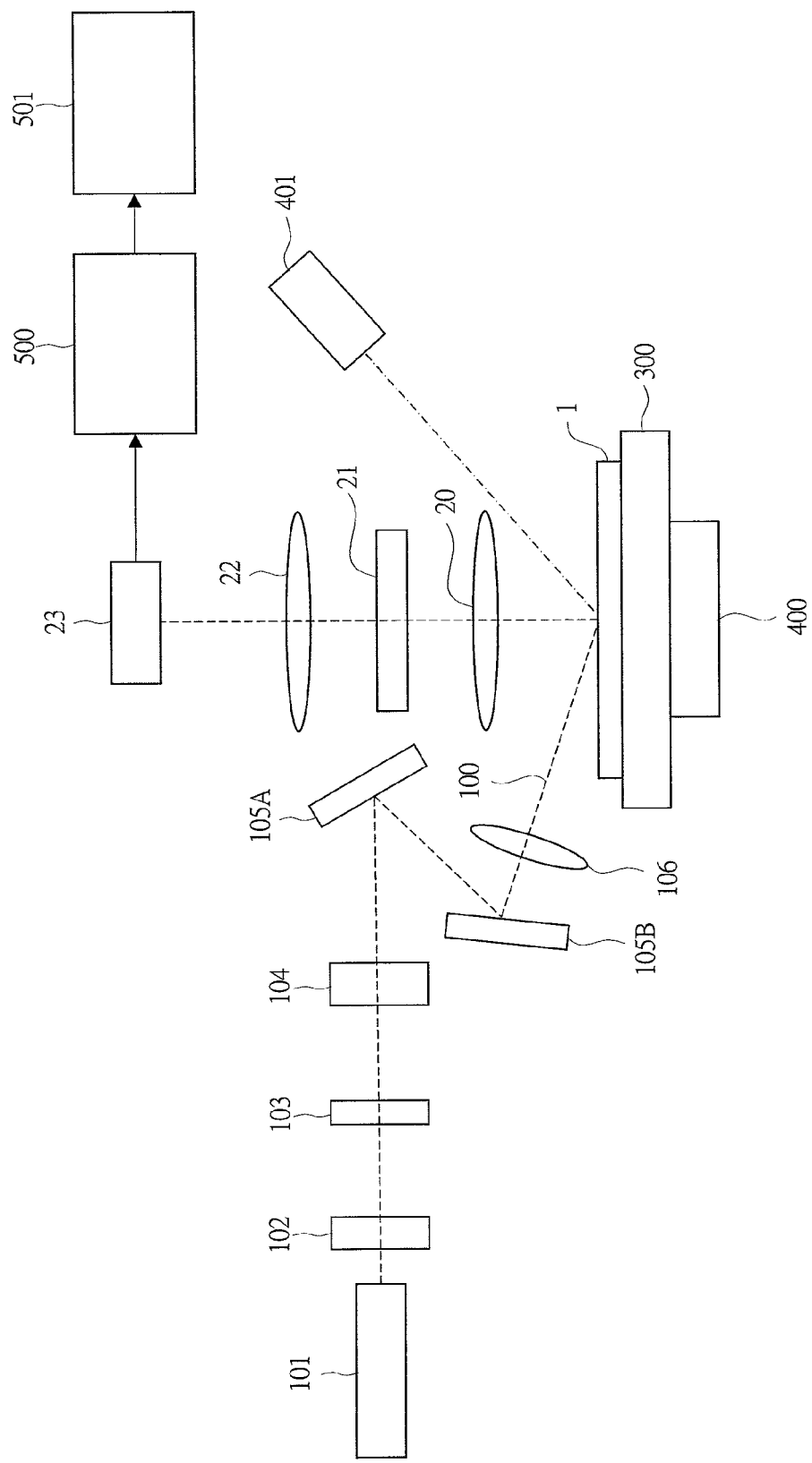
FIG. 1 is a diagram of a structure of a general dark-field defect inspecting apparatus.

FIG. 1 is a diagram of a structure of a general dark-field defect inspecting apparatus. Details about the dark-field defect inspecting apparatus will be described with reference to the drawing.

The general dark-field defect inspecting apparatus is configured to include an objective lens 20, a spatial filter 21, an imaging lens 22, a sensor 23, a laser 101, a beam expander 102, an attenuator 103, a polarization control element 104, mirrors 105A and 105B, a lens 106, an XY stage 300, a Z stage 400, an inspection-object height measuring unit 401, a signal processing unit 500, and a monitor 501.

The objective lens 20 is an objective lens collecting, from a direction (upward) perpendicular to a normal direction of an inspection subject 1, light scattered or diffracted from a foreign substance, a defect, or a pattern on the inspection subject with irradiation of illumination light 100.

The inspection subject 1 is a semiconductor device or the like to be inspected by this dark-field defect inspecting apparatus. The inspection subject 1 is placed on the XY stage 300.

The objective lens 20 is a lens for collecting scattered light from the inspection subject 1.

When a pattern formed on the inspection subject 1 is in a form of a repeated shape, diffracted light occurring from the repeated pattern is collected at an exit pupil of the objective lens 20 at regular intervals. The spatial filter 21 is a filter of light-shielding this repeated pattern at the exit pupil.

The imaging lens 22 is a lens for imaging, on the sensor 23, scattered light or diffracted light from a portion (for example, a failure occurring portion) other than the repeated pattern, the light passing through the spatial filter 21.

The sensor 23 is an optical sensor for sending the image imaged by collecting light by the imaging lens 22 to the signal processing unit 500 as electronic information. As a type of the optical sensor, a CCD or a CMOS is general, but any type can be used herein.

Hereinafter, the objective lens 20, the spatial filter 21, the imaging lens 22, and the sensor 23 are collectively referred to as a "detection system".

The laser 101 irradiates the inspection subject 1 with the illumination light 100 for forming a desired beam. With this illumination light 100, the surface of the inspection subject 1 is illuminated from a direction at an angle with respect to the normal direction of the inspection subject, thereby forming the desired beam on the inspection subject 1.

The beam expander 102 is a laser beam expander expanding the illumination light 100 to parallel light flux at a predetermined magnification.

The attenuator 103 is an attenuator for controlling a light amount and intensity of the illumination light 100 after passing through the expander 102.

The polarization control element 104 is an element changing the rotation of a polarizer or a wave plate, or the orientation of molecules of liquid crystals by ON/OFF voltage control to switch the polarizing direction of light incident to the element and control the polarization state.

The mirrors 105A and 105B are reflecting mirrors for adjusting an irradiation angle when the inspection subject 1 is irradiated with the illumination light 100 after polarization control (control over the phase and amplitude of an electric field).

The lens 106 is a lens for causing the illumination light 100 to converge to an irradiation point immediately before irradiation of the inspection subject 1.

In the following, these laser 101, beam expander 102, attenuator 103, polarization control element 104, mirrors 105A and 105B are collectively referred to as an "illumination system".

The XY stage 300 is a stage for having the inspection subject 1 placed thereon. The inspection subject 1 is scanned as being moved on the XY stage 300 in a plane direction.

The Z stage 400 is a stage for moving an inspection reference surface (a surface where the inspection subject 1 is placed) of the XY stage 300 in a vertical direction (Z direction).

The inspection-subject height measuring unit 401 is a measuring instrument for measuring the height of the inspection reference surface of this XY stage 300 and the inspection subject 1. By the Z stage 400 and the inspection-subject height measuring unit 401, an automatic focusing function of automatically performing focus positioning is provided.

The signal processing unit 500 is a circuit for converting image data received from the sensor 23 to a displayable state on the monitor 501.

Next, an entire operation will be described.

First, with the illumination light 100 from the laser 101, the surface of the inspection subject 1 is illuminated from a direction with an angle with respect to the normal direction of the inspection subject to form a desired beam on the inspection subject 1.

Light scattered or diffracted from a foreign substance, a defect, or a pattern on the inspection subject with the beam is collected by the objective lens 20 from the direction (upward) perpendicular to the normal direction of the inspection subject.

When a pattern formed on the inspection subject 1 is in a form of a repeated shape, diffracted light occurring from repeated patterns is collected at the exit pupil of the objective lens at regular intervals, and is therefore light-shielded by the spatial filter 21 placed on a pupil plane.

On the other hand, the scattered light or diffracted light from portions other than the repeated pattern passes through the spatial filter 21 to be guided to the imaging lens 22 and imaged on the sensor 23.

The inspection subject 1 is placed on the XY stage 300. By scanning with this XY stage 300, two-dimensional images of scattered light from the inspection subject 1 are obtained. Here, a distance between the inspection subject 1 and the objective lens 20 is measured by the inspection-subject height measuring unit 401 and adjusted by the Z stage 400.

The two-dimensional images obtained by the sensor 23 are classified by the signal processing unit 500 for each foreign substance type or each defect type, where sizes of foreign substances or defects are found, and results are then displayed on the monitor 501.

In the structure of the dark-field defect inspecting apparatus described above, a dedicated function of monitoring the apparatus state is not provided, and apparatus calibration is performed by using scattered light from a wafer for calibration. However, with complex apparatus structure and many portions to be adjusted, it is very difficult to perform apparatus calibration by using a scattering phenomenon, for which mathematical description is difficult.

(First Embodiment)

In comparison with the existing aspect described above, a first embodiment of the present invention is described.

Figure 2:
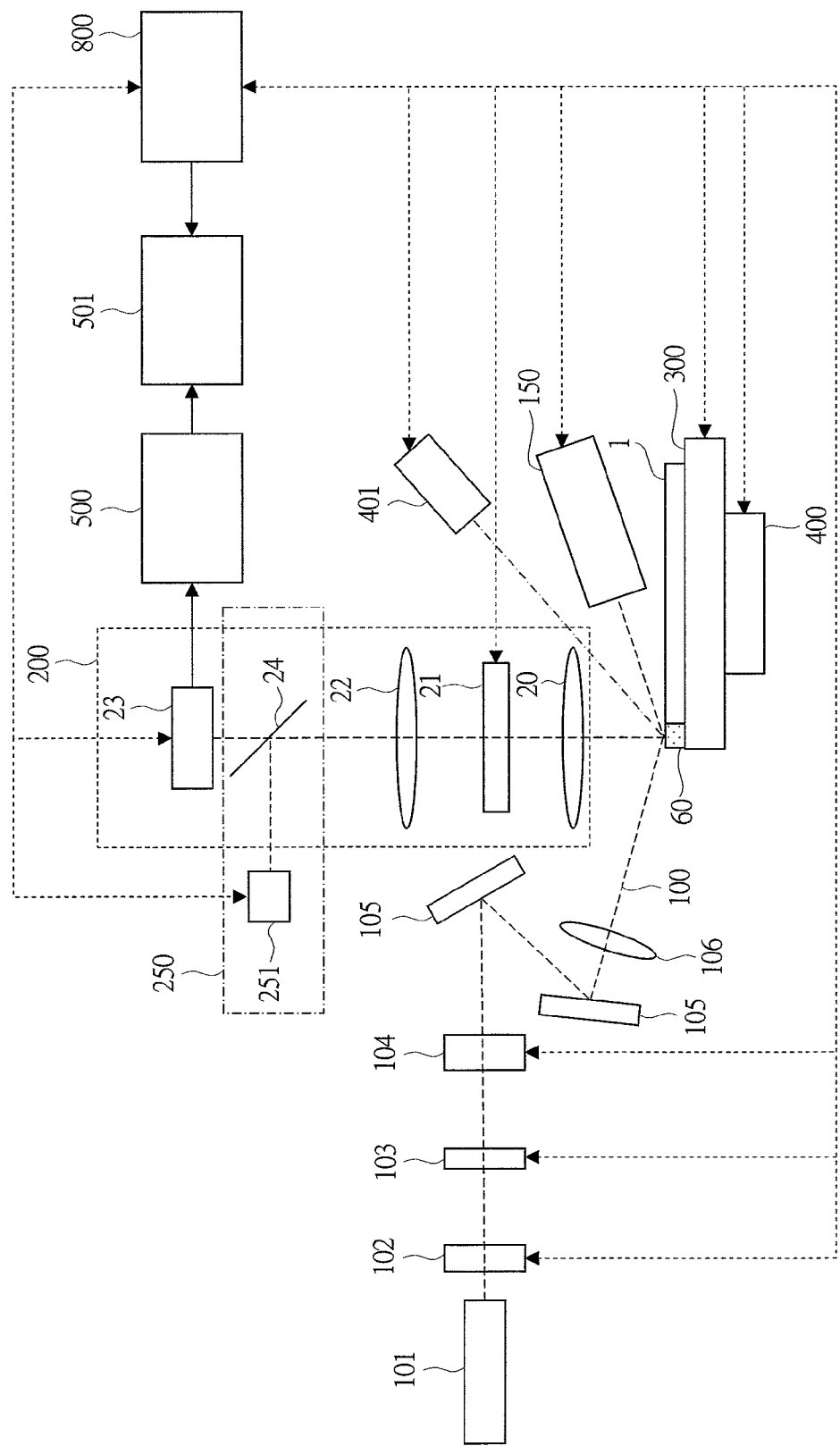
FIG. 2 is a diagram of the structure of a dark-field defect inspecting apparatus according to a first embodiment of the present invention.

FIG. 2 is a diagram of a structure of a dark-field defect inspecting apparatus according to the first embodiment of the present invention. In the dark-field defect inspecting apparatus according to the present embodiment, in addition to the structure of the dark-field defect inspecting apparatus of FIG. 1, an illumination-system monitoring unit 150, a detection-system monitoring unit 250, and a control unit 800 are provided. Note that the details described in FIG. 1 represent the same processes as those of the present drawing. Description of individual components and the entire operation are omitted.

The illumination-system monitoring unit 150 is a sensor circuit measuring the state of illumination light. In the dark-field defect inspecting apparatus, the inspection subject is irradiated with illumination light, and its scattered light is detected. Here, scattered light caused by the inspection subject depends on an intensity distribution and a polarization state distribution of the illumination light. Therefore, the illumination light state is required to be monitored. The illumination-system monitoring unit 150 has a two-dimensional polarization measuring function of measuring a spatial two-dimensional distribution with a polarization state and intensity of the light. The two-dimensional polarization measuring function is configured of a polarizing element such as a polarizer, a wave plate, and a detector. A desired polarization component of light to be measured, which is specular reflection light of the illumination light is extracted by the polarizing element. From a signal detected by the detector in the extracted polarization component, an intensity distribution and a polarization state distribution of the light to be measured are determined.

The detection-system monitoring unit 250 is a sensor circuit of measuring the state of the detection system. The detection-system monitoring unit 250 includes a half mirror 24 and a sensor 251.

The control unit 800 is a control circuit comparing the values obtained by the illumination-system monitoring unit 150 and the detection-system monitoring unit 250 to perform feedback control.

Figure 3:
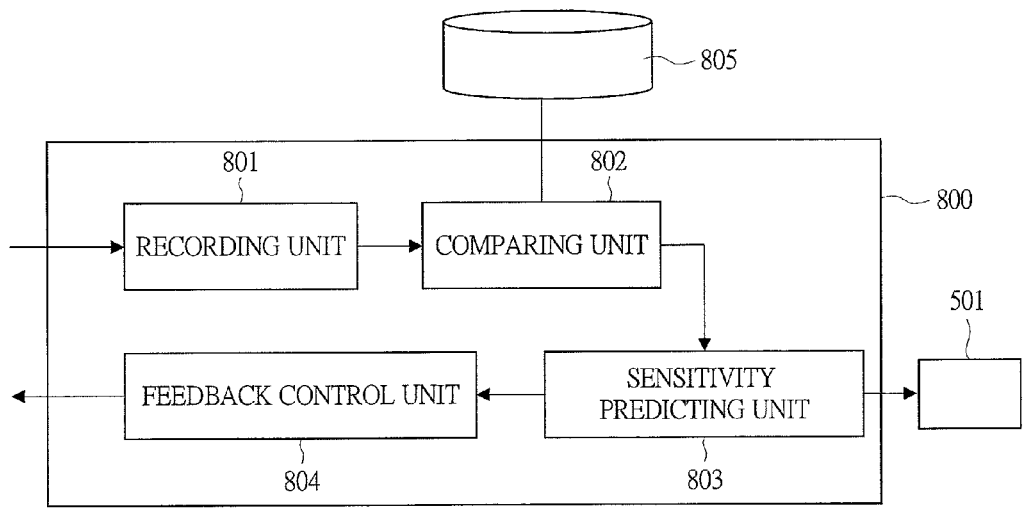
FIG. 3 is a block diagram of an inner structure of a control unit according to the first embodiment of the present invention.

FIG. 3 is a block diagram of an inner structure of the control unit 800 according to the first embodiment of the present invention.

The control unit 800 is configured to include a recording unit 801, a comparing unit 802, a sensitivity predicting unit 803, and a feedback control unit 804.

The recording unit 801 is a circuit recording the monitored data of the illumination-system monitoring unit 150 and the detection-system monitoring unit 250.

The comparing unit 802 is a circuit comparing the data recorded in the recording unit 801 with an ideal or predetermined value in a database 805. Prior to processing at the comparing unit 802, the characteristics of a light source and elements at the time of monitoring are calculated in advance.

The sensitivity predicting unit 803 is a circuit estimating and predicting a current apparatus sensitivity from a difference between the recorded data and the ideal value.

The feedback control unit 804 is a circuit performing feedback onto each operating unit of the apparatus according to a predicted sensitivity predicted by the sensitivity predicting unit 803.

The database 805 is a database of ideal or predetermined values for use by the comparing unit 802. In this database 805, ideal or predetermined values are input through theoretical calculation, optical simulations, and others. Here, in an optical simulator, the inspection subject is modeled, an intensity of scattered light intensity and others occurring from the inspection subject depending on the condition of the illumination optical system are derived, and an optical intensity detected in an sensor is calculated. Parameters of the ideal or predetermined values in this database 805 include information about an intensity distribution of the illumination optical system, a polarization state distribution, a focal length of the imaging lens 22, sensitivity of the sensor 23, and others. As for these parameters, their characteristics are required to be ascertained in advance.

Figure 4:
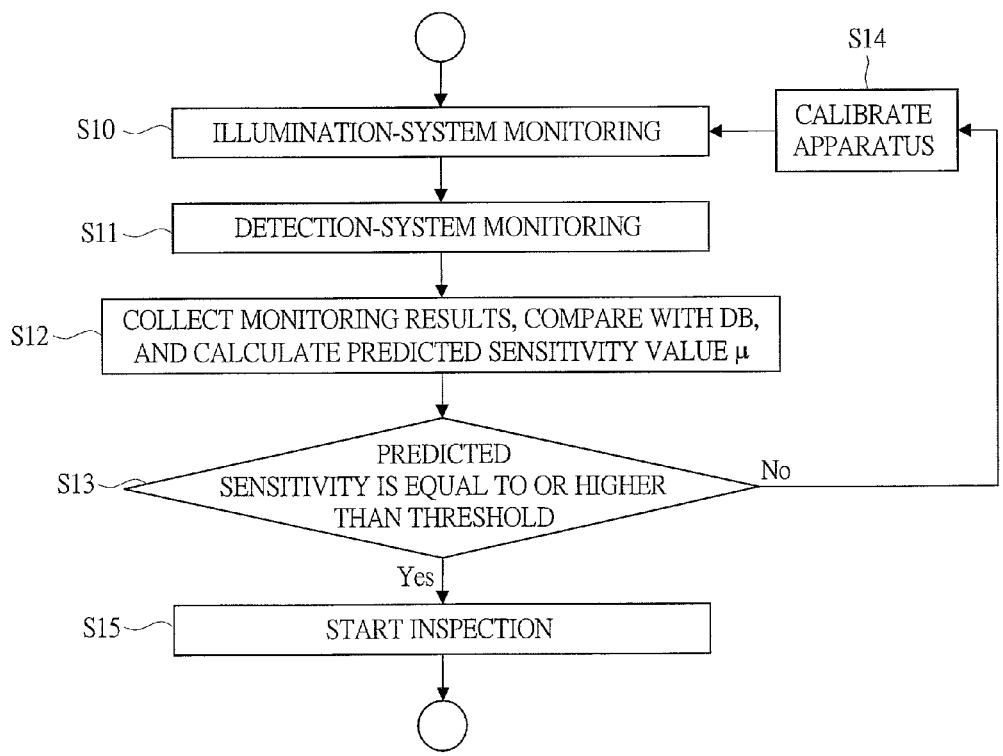
FIG. 4 is a flowchart of a monitoring process procedure in the dark-field defect inspecting apparatus according to the first embodiment of the present invention.

FIG. 4 is a flowchart of a monitoring process procedure in the dark-field defect inspecting apparatus according to the first embodiment of the present invention.

First, the state of the illumination system is monitored by the illumination-system monitoring unit 150 (step S10). Also, the state of the detection system is measured by the detection-system monitoring unit 250 (step S11). The measurement results obtained at step S10 and step S11 are sent to the comparing unit 802. The comparing unit 802 compares these measurement results with respective ideal values in the database 805 and, furthermore, predicts a detection sensitivity from a "deviation" occurring between the ideal value and the measurement result (step S12). Then, it is determined whether the predicted detection sensitivity is larger or smaller than an arbitrarily set threshold (step S13).

When the predicted sensitivity is equal to or lower than the threshold, calibration of the optical system is performed (step S14). Here, if all calibration-required portions can be automatically controlled, all calibrating operations may be automatically performed. Here, the portions to be calibrated are determined in advance through theoretical calculation or an optical-system simulation.

On the other hand, when the predicted sensitivity is equal to or higher than threshold, inspection of the illumination system and the detection system is started (step S15).

After these processes are performed, the procedure returns to the step S10 again.

Figure 5:
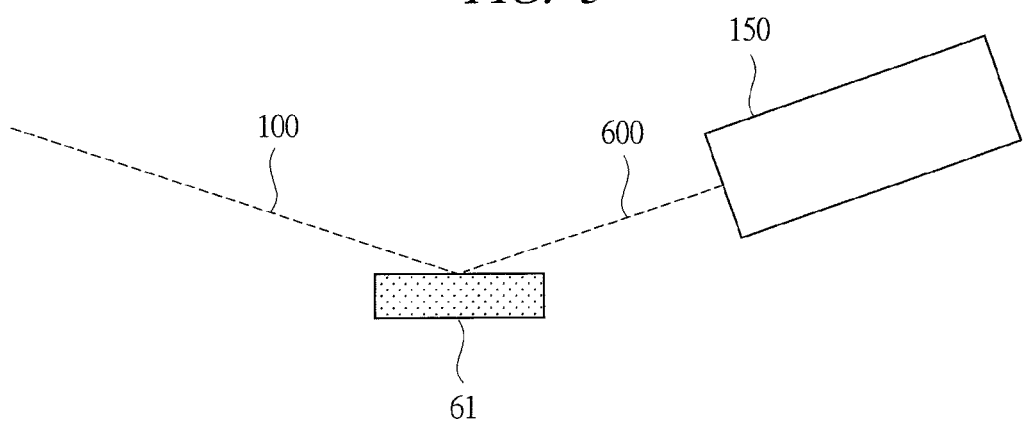
FIG. 5 is a conceptual diagram illustrating a concept of the monitoring process by an illumination-system monitoring unit.

The monitoring process of the illumination-system monitoring unit 150 is described in detail below. FIG. 5 is a conceptual diagram illustrating a concept of the monitoring process by the illumination-system monitoring unit 150.

First, prior to irradiation of the inspection subject 1, a reference mirror 61 placed on the XY stage 300 is irradiated with the illumination light 100. The reference mirror 61 is a reflecting mirror having fewer asperities on the surface compared with a foreign substance assumed to be present on the inspection subject 1 and a defect of the inspection subject 1 that is an inspection target. A size of the reference mirror 61 is larger than the spread of the illumination light.

A two-dimensional polarization state distribution (including an intensity distribution) of specular reflected light 600 reflected from the reference mirror 61 upon irradiation is measured by the illumination-system monitoring unit 150. By using the reference mirror 61 with its material and illumination angle of elevation known, a Fresnel coefficient giving a change in amplitude and phase due to reflection is calculated by the control unit 800 or the illumination-system monitoring unit 150. From the intensity distribution and the polarization state distribution of the specular reflected light 600, an intensity distribution and a polarization state distribution of the illumination light 100 are calculated.

As described above, by monitoring the two-dimensional polarization distribution (including an intensity distribution) of the illumination light by using measurement and theoretical calculation, a predicted sensitivity $\mu$, which will be described further below, can be accurately found.

To calibrate the intensity distribution of the illumination light 100, any of the illumination system, such as the laser 101, the beam expander 102, the attenuator 103, the polarization control element 104, and the mirrors 105A and 105B, is adjusted. To calibrate the polarization distribution, the polarization control element 104 or the like is adjusted.

As described above, when illumination-system monitoring is performed, parameters for use in calibration are obtained by using the specular reflected light 600.

Next, the monitoring process of the detection-system monitoring unit 250 is described in detail below. In the detection-system monitoring unit 250, how a point source of light or arbitrary diffracted light is detected is measured by the half mirror 24 and the sensor 251 to ascertain the state.

First, detection-system monitoring with a point source of light is described.

Light emitted from a point source of light is introduced to the detection system, and an image of the point source of light imaged on the sensor 23 is observed by the objective lens 20 and the imaging lens 22, thereby monitoring a resolving power, which is a lens imaging characteristic, a change in wave aberration after passage through the lens, and others are monitored. Also, by measuring a point image as the height of the stage is being raised and lowered, it can be confirmed whether the Z stage 400 works properly. Furthermore, while the XY stage 300 is being moved, the Z stage 400 is raised and lowered at an arbitrary position. In this state, by detecting a signal of the inspection subject height measuring unit 401, fluctuations of the XY stage 300 in a height direction due to the movement can be measured. After the lens, the XY stage 300, and the Z stage 400 are adjusted, a point image is incident to the sensor 23 to calibrate a gain.

Here, the point source of light collects light flux so that they are at a spot on a diffusion plate, thereby obtaining a point source of light from the diffusion plate for use. Here, the diffusion plate for use preferably has a small angle of elevation of a scattered light amount and azimuth dependency (ideally, zero). Note that although the diffusion plate is used in the present embodiment, a microsphere having a diameter smaller than the wavelength may be used in place of the diffusion plate and be irradiated with illumination light for obtainment.

Next, detection-system monitoring using diffracted light is described.

The diffracted light diffracting in a specific direction is generated by an arbitrary diffraction grating in place of a diffusion plate or microsphere. At the exit pupil, point images are regularly arranged in a direction depending on the direction of the diffracted light. A driving unit of the spatial filter and an actual distance travelled are monitored and calibrated so as to light-shield this regular arrangement of point images, thereby precisely eliminating a specific periodic structure of the inspection subject.

As for the diffraction grating, one having a plurality of grooves of different directions and periods is prepared, thereby monitoring the operation of the spatial filter in more detail.

A diffusion plate for generation of a point source of light and a diffraction grating for generation of diffracted light are both put on the XY stage 300, and are used each as an element for monitoring before or after an inspection subject is placed.

Figure 6:
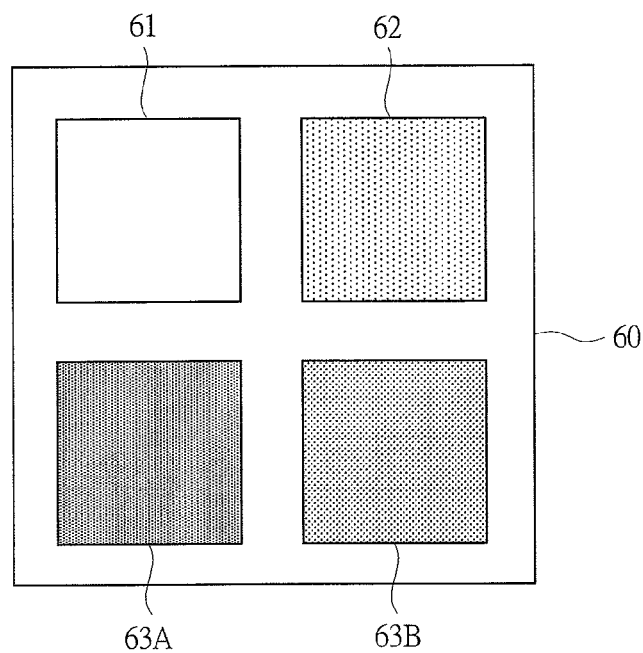
FIG. 6 is a diagram of a chip for monitoring for use in monitoring an illumination system and a detection system.

FIG. 6 is a diagram of a chip for monitoring 60 for use in monitoring the illumination system and the detection system.

This monitoring chip 60 includes the reference mirror 61 for use in illumination-system monitoring, a diffusion plate 62 for use in generation of a point source of light in detection-system monitoring, and diffraction gratings 63A and 63B for use in generation of diffracted light in detection-system monitoring. By combining these into one, the stage moving amount is decreased, thereby efficiently monitoring the apparatus.

Next, apparatus sensitivity prediction and apparatus calibration using the monitoring results of the apparatus state are described.

The inspection sensitivity of the inspecting apparatus indicates the size of a foreign substance or defect detectable on a semiconductor wafer or a scattering light intensity itself from the foreign substance or defect. When the apparatus state is deviated from an ideal state, the inspection sensitivity is decreased. Thus, an index indicating an inspection sensitivity is calculated from a difference between a physical quantity representing the apparatus state monitored and an ideal state of that physical quantity, and apparatus calibration is performed so that the inspection sensitivity is kept equal to or higher than a certain value.

Here, "a physical quantity representing the apparatus state" indicates an intensity distribution of the illumination optical system, a polarization state distribution, a detection-lens focal length, a detection sensitivity, and others. Also, monitoring of each physical quantity is performed during measurement of the inspection subject or always.

Here, as an ideal or predetermined value of the physical quantity to be monitored, all or any one of the following is used: a design value, a theoretical calculation value, and a value calculated from an optical simulation.

Figure 7:
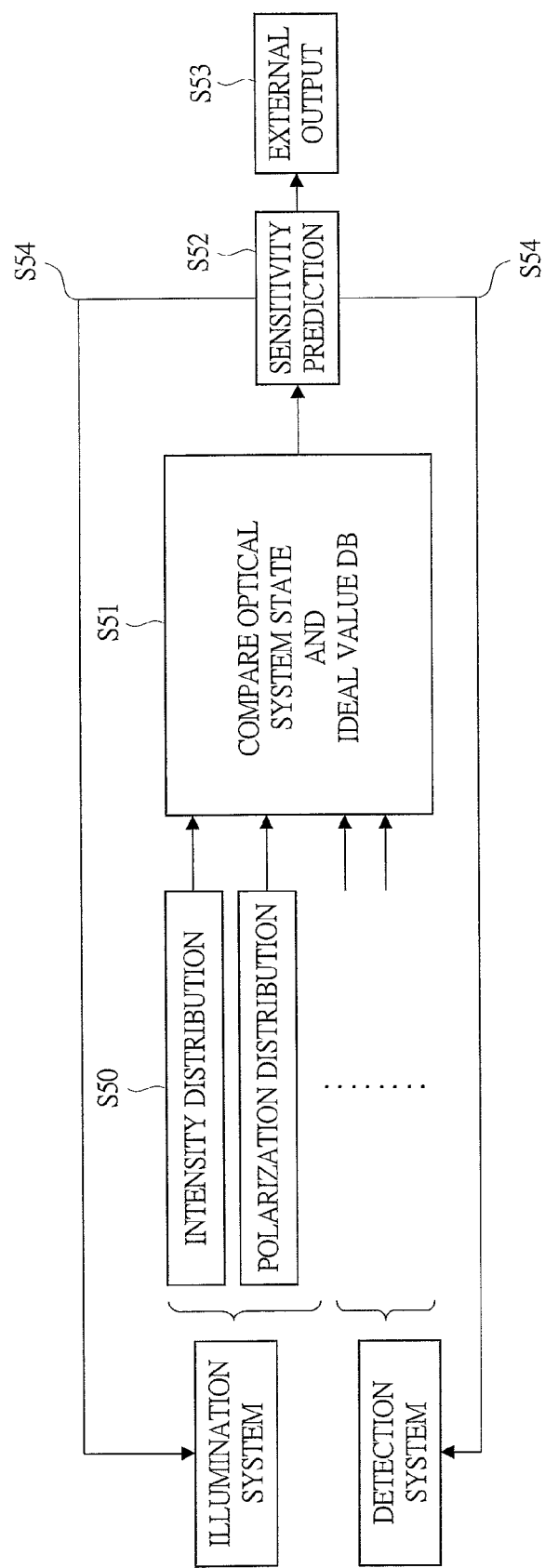
FIG. 7 is a conceptual diagram illustrating an example of an apparatus calibrating procedure.

FIG. 7 is a conceptual diagram illustrating an example of an apparatus calibrating procedure.

A physical quantity through monitoring each of the illumination system and the detection system is taken as Fi, and this is transmitted to the comparing unit 802 (step S50). With a root-mean-square value of a difference between the physical quantity Fi and an ideal value Gi being weighted with Ai, that is, $$Ei = Ai(Fi - Gi)^2 \quad \text{(Equation 1)},$$

comparison with the ideal-value database is performed (step S51).

A deviation of every monitoring value from its ideal one is represented as $$E = \Sigma Ei \quad \text{(Equation 2)}.$$

By using an index regarding sensitivity represented by E found in (Equation 2), that is, $$\mu = 1/(1-E) \quad \text{(Equation 3)},$$

the sensitivity predicting unit 803 predicts a sensitivity (step S52).

By externally outputting this index via the monitor 501, the index can be taken as a guideline for an operator to visually determine an apparatus state (step S53). Also, a predetermined threshold may be set in advance for $\mu$ and, when $\mu$ becomes equal to or smaller than the threshold, an apparatus parameter may be calibrated (step S54).

Figure 8:
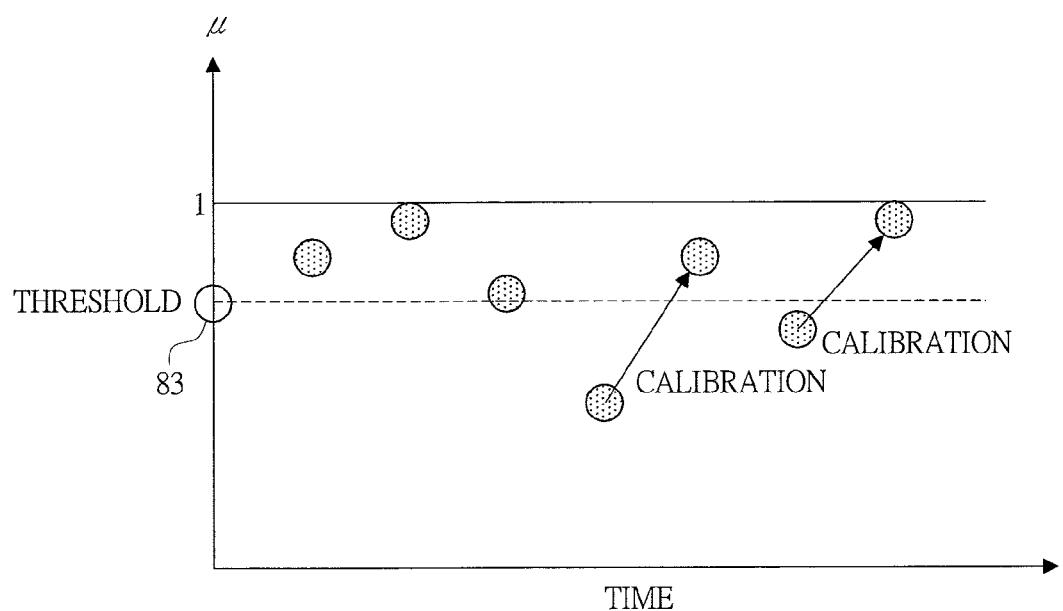
FIG. 8 is a graph regarding a process of calibrating an apparatus parameter with a threshold.

FIG. 8 is a graph regarding a process of calibrating the apparatus parameter with the threshold. In the drawing, a threshold 83 is taken as a reference. Here, the threshold 83 is a parameter regarding apparatus performance, and its value is determined by the use purpose of the apparatus, such as stability inspection. When a value of a high-sensitivity inspection micro is equal to or smaller than the threshold 83, $\mu$ value is calibrated so as to be closer to 1. After calibration, monitoring is again performed, and effectiveness of the effect of calibration is checked.

Figure 9:
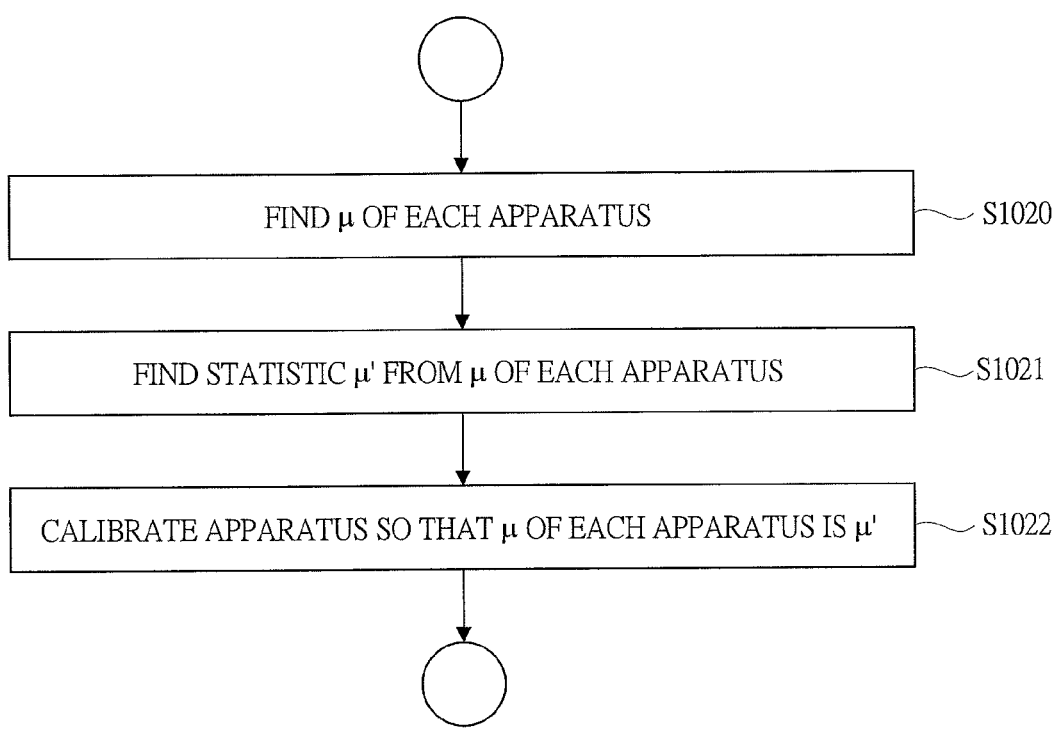
FIG. 9 is a flowchart illustrating a process procedure of uniformization of performance among a plurality of dark-field defect inspecting apparatuses according to the first embodiment of the present invention.

The sensitivity (predicted sensitivity) $\mu$ predicted by the sensitivity predicting unit 803 can be used for uniformization of performance between apparatuses. That is, for every index representing a detection sensitivity, completely matching the performances of a plurality of dark-field defect inspecting apparatuses is not practical. Thus, uniformization of performance is sought with a statistic of predicted sensitivity being taken as a target value. FIG. 9 is a flowchart illustrating a process procedure of uniformization of performance among a plurality of dark-field defect inspecting apparatuses according to the first embodiment.

First, the predicted sensitivity $\mu$ is derived for each of the plurality of dark-field defect inspecting apparatuses (step S1020). From the predicted sensitivity $\mu$ for each of the plurality of dark-field defect inspecting apparatuses, a statistic $\mu'$ is taken as a guideline for sensitivity (step S1021). Then, the feedback control unit 804 of each apparatus performs apparatus calibration so that $\mu$ of each apparatus is $\mu'$ (step S1022).

Also, in addition to parameters regarding apparatus calibration for illumination light, the detection system, and others, parameters of temperature, atmospheric pressure, and moisture, which are parameters representing the environment inside the apparatus, are also monitored at the same time. In general, the characteristics of an optical element fluctuate depending on the usage environment. For example, a refractive index of glass forming a lens has temperature dependency, and the focal length, wave aberration, and others fluctuate depending on the temperature near the lens. Therefore, in adjustment of the optical element, the parameters regarding the apparatus environment described above are required to be taken into consideration.

All or part of monitored physical quantity, changes of the predicted sensitivity $\mu$ with time, and time for measuring the inspection subject are recorded and are utilized for ascertainment of the state of the apparatuses and defect prediction. Note that monitoring of each physical quantity is performed during measurement of the inspection subject, always, regularly such as once a week, or upon power-on of the apparatus.

FIG. 10 is a conceptual diagram illustrating what type of defect is conceivable depending on the behavior of the predicted sensitivity $\mu$ of the dark-field defect inspecting apparatus.

Figure 10A:
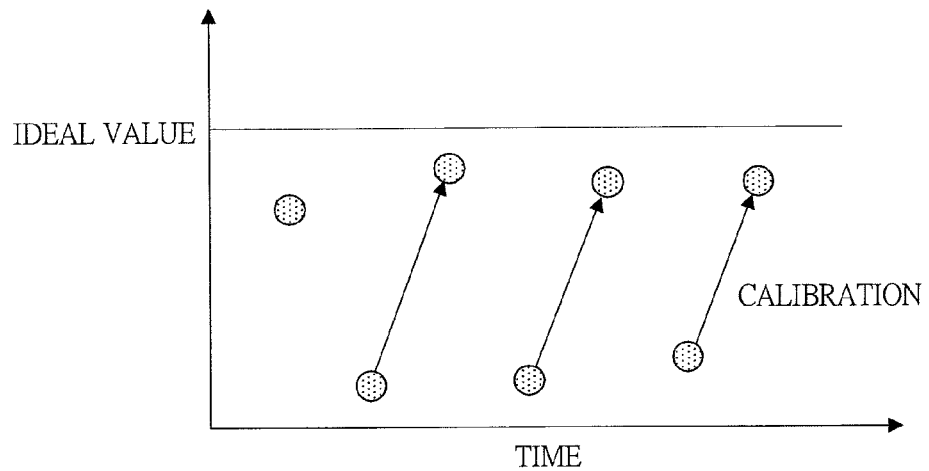
FIG. 10 is a conceptual diagram illustrating what type of defect is conceivable depending on the behavior of a predicted sensitivity μ of the dark-field defect inspecting apparatus.
Figure 10B:
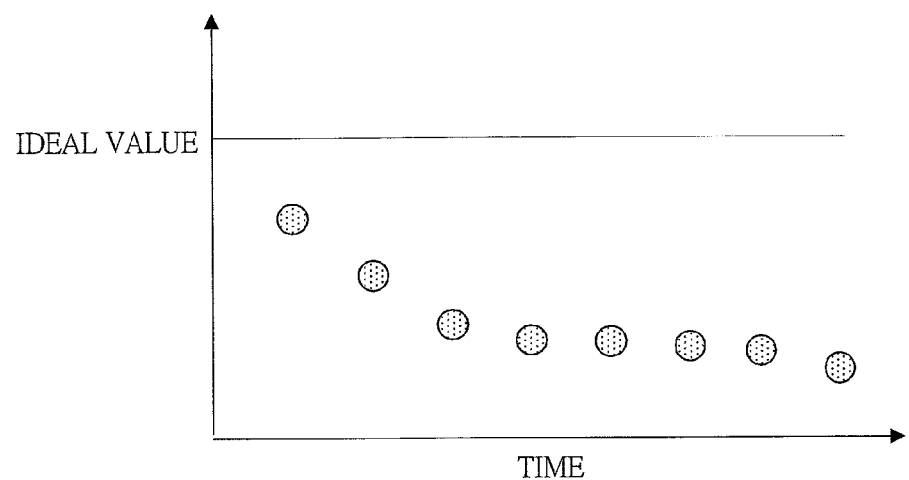
Figure 10C:
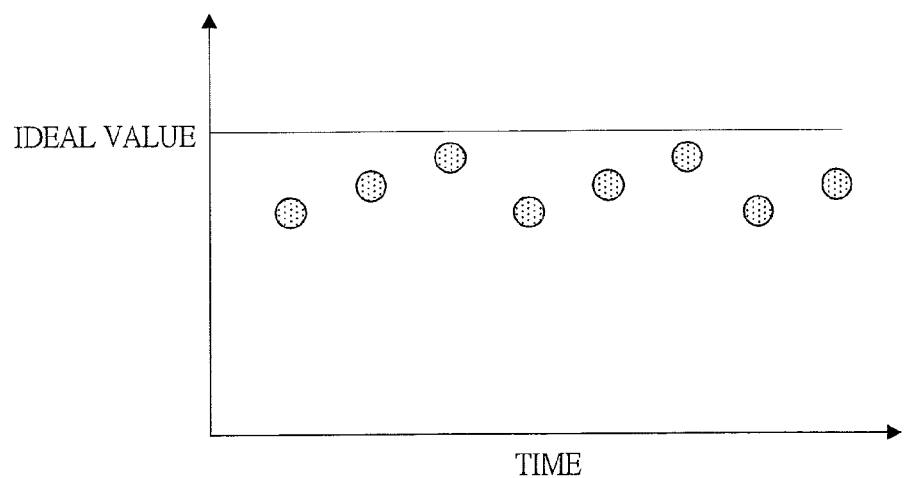

For example, when the monitored value is decreased in a short period of time even with repeated calibration as illustrated in FIG. 10A or when the monitored value is not improved even with calibration as illustrated in FIG. 10B, some problem is assumed to be included in the apparatus itself. Therefore, the operator (or an apparatus administrator) can sense the necessity of part replacement or the like. Also, when the monitored value changes temporally and periodically as in FIG. 10C, a fluctuation factor of the monitored value can be thought to reside either inside or outside of the apparatus.

Figure 11:
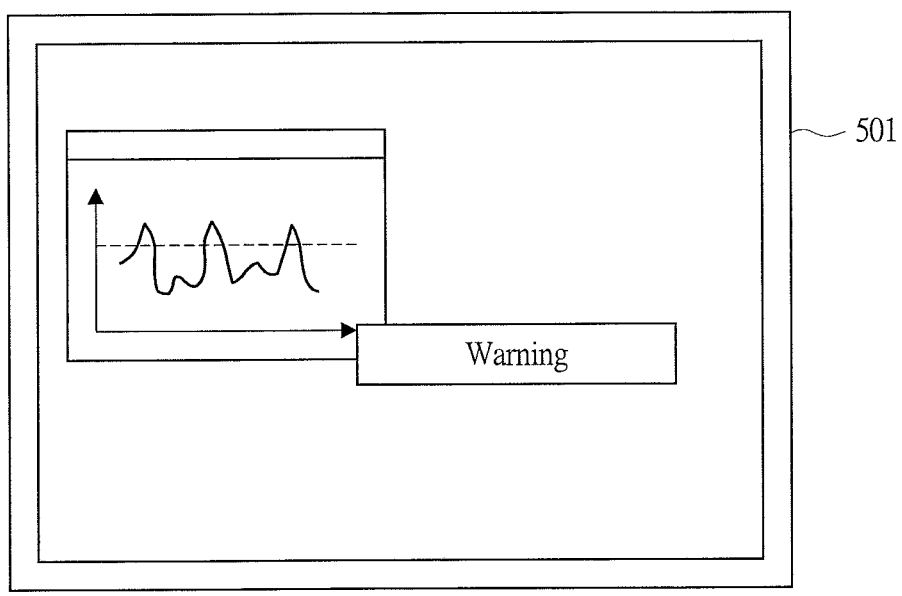
FIG. 11 illustrates a screen informing a warning in the first embodiment of the present invention.

When the predicted sensitivity μ becomes equal to or lower than a predetermined count threshold within a short period of time, a warning may be issued on the monitor 501. FIG. 11 illustrates a screen informing a warning in the present embodiment.

In this manner, not only by deriving the predicted value μ for each individual dark-field defect inspecting apparatus for calibration but also by finding the statistic μ' from the predicted values μ of the plurality of dark-field defect inspecting apparatuses and calibrating each individual dark-field defect inspecting apparatus so that the sensitivity is close to the statistic μ', the difference in sensitivity between apparatuses can be reduced.

Also, in place of the statistic μ', a physical quantity representing the apparatus state derived from an optical simulation, and a detection sensitivity estimated from that physical quantity may be used as a guideline for apparatus calibration.

Modification examples of the present embodiment are described below.

Figure 12:
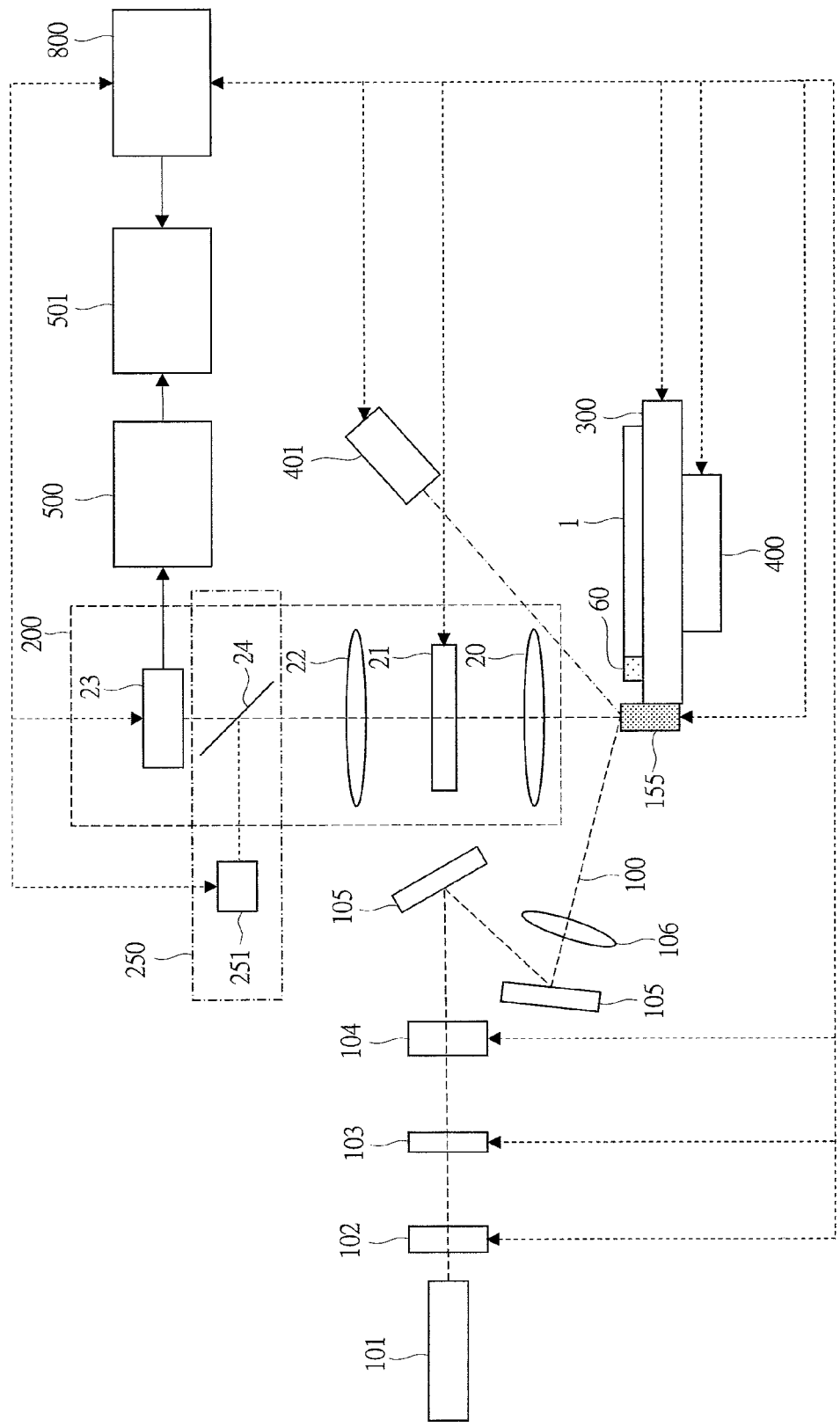
FIG. 12 is a diagram of a structure of another dark-field defect inspecting apparatus according to the first embodiment of the present invention.

FIG. 12 is a diagram of a structure of another dark-field defect inspecting apparatus according to the first embodiment of the present invention. In the structure of the dark-field defect inspecting apparatus in this drawing, the point-source-light generating unit 155 for use in detection-system monitoring is provided on an XY stage 300 side part. Monitoring the detection system by using this point-source-light generating unit 155 is different from the dark-field defect inspecting apparatus of FIG. 2.

Figure 13:
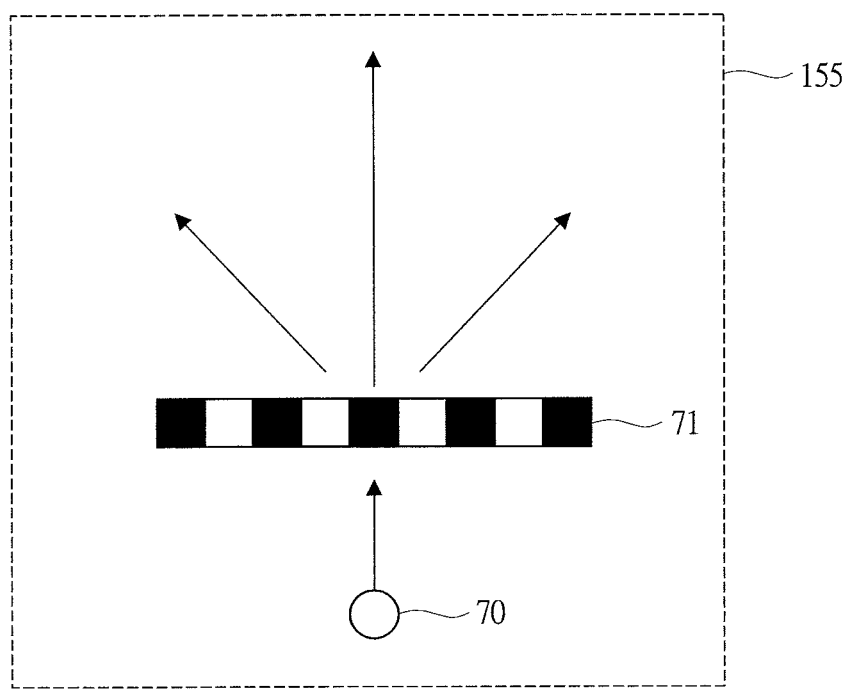
FIG. 13 is a diagram of a structure of a point-source-light generating unit.

FIG. 13 is a diagram of the structure of this point-source-light generating unit 155.

In the point-light-source generating unit 155, a light source 70 and a transmission-type spatial filter 71 are included. Light output from the light source 70 is incident to the detection system via the transmission-type spatial filter 71.

Figure 14:
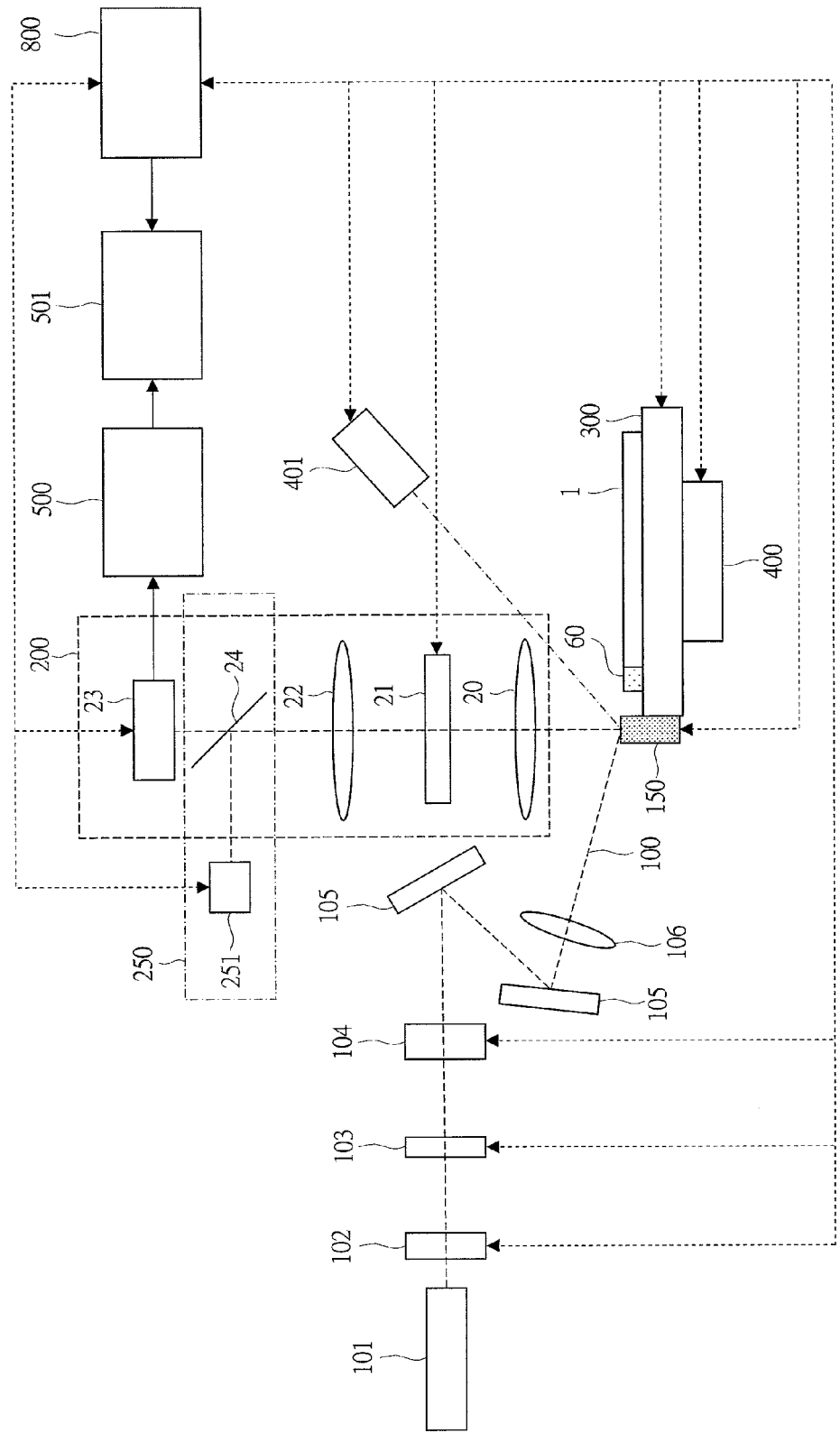
FIG. 14 is a diagram of a structure of another dark-field defect inspecting apparatus according to the first embodiment of the present invention.

Also, FIG. 14 is a diagram of the structure of another dark-field defect inspecting apparatus according to the first embodiment of the present invention. In the dark-field defect inspecting apparatus in this drawing, a two-dimensional polarization distribution of illumination light is directly measured on the XY stage 300. That is, the illumination-system monitoring unit 150 is provided on an XY stage 300 side part, and by using this, a two-dimensional polarization distribution of illumination light is monitored during measurement. Compared with the scheme of using the specular reflected light 600, the state of illumination light can be more accurately monitored. Note that, in this case, the diffusion plate 62 for use in point-light-source generation in detection-system monitoring and the diffraction gratings 63A and 63B for use in diffracted light generation in detection-type monitoring are enough to be provided on the chip for monitoring 60, and the reference mirror 61 is not required.

Figure 15:
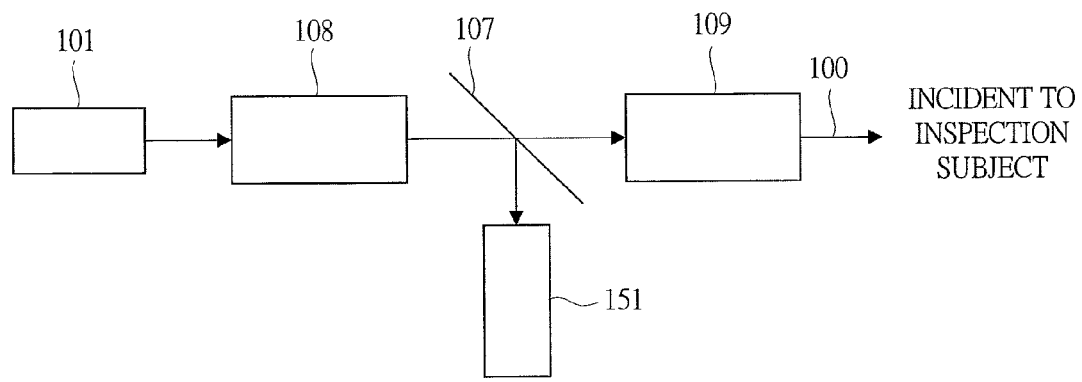
FIG. 15 is a diagram of a structure of illumination-system monitoring of another dark-field defect inspecting apparatus according to the first embodiment of the present invention.

FIG. 15 is a diagram of a structure of illumination-system monitoring of another dark-field defect inspecting apparatus according to the first embodiment of the present invention. In the illumination-system monitoring in the drawing, a height distribution and a polarization state distribution are monitored before the illumination system arrives at the surface to be inspected, and the state on the inspection surface is derived by theoretical calculation. In the course of the illumination system, one is taken as the illumination light 100 by using the half mirror 107 or the like, and the other is taken as light for monitoring, and they are detected by the illumination-system monitoring unit 151.

Optical element groups 108 and 109 are each formed of any of the beam expander 102, the attenuator 103, the polarization control element 104, the mirror 105, and the lens 106.

In the illumination-system monitoring unit 151, a two-dimensional polarization state distribution is measured and, from the optical characteristics of the polarizing element, the mirror, and others, which are elements after passage through the half mirror 107, the state of the illumination light 100 at the surface to be inspected is calculated. Here, the polarization state of light (including an intensity distribution) can be displayed by using 1×4 vectors, which are referred to as Stokes vectors. Also, the optical element can be described as a 4×4 matrix connecting the Stokes vectors, which is referred to as a Muller matrix. By using these Stokes vectors and Muller matrix, the control unit 800 or the illumination-system monitoring 151 calculates a polarization state of the illumination light.

A largest merit of this embodiment is that real-time monitoring can be made, because light is branched and detected in an optical path. Note that, even in the dark-field defect inspecting apparatus in this drawing, the reference mirror 61 is not required in the chip for monitoring 60.

(Second Embodiment)

Next, a second embodiment of the present invention is described.

The structure of the second embodiment is identical to the structure of the dark-field defect inspecting apparatus illustrated in FIG. 2. A difference from the first embodiment is a process at the control unit 800.

In the present embodiment, the control unit 800 controls the illumination-system monitoring unit 250 monitoring the intensity and polarization state of the illumination light 100, imaging performance of the detection system, driving information of the spatial filter 21, and the detection-system monitoring unit 250 monitoring automatic focusing or the like formed of the XY stage 300, the Z stage 400, and the inspection-subject height measuring unit 401.

Figure 16:
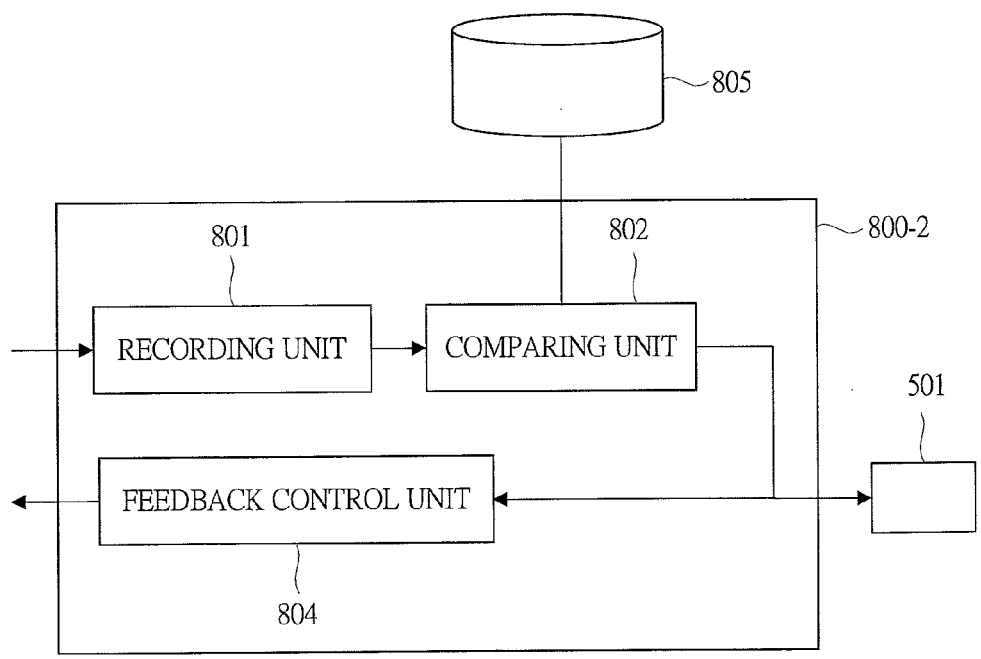
FIG. 16 is a block diagram of an inner structure of a control unit according to a second embodiment of the present invention.

FIG. 16 is a block diagram of an inner structure of a control unit 800-2 according to the present embodiment.

This control unit 800-2 includes the recording unit 801, the comparing unit 802, and the feedback control unit 804.

The recording unit 801 is a circuit recording monitored data.

The comparing unit 802 is a circuit comparing the record data recorded in the recording unit 801 with the database 805 that associates an apparatus state calculated in advance through theoretical calculation, an optical simulation, or the like with monitoring results.

The feedback control unit 804 is a circuit finding a value in the database 805 with a small difference from the measurement value, taking an apparatus state assumed when the value in the database is calculated as an actual apparatus state, and performing feedback control on each part of the apparatus so as to achieve an ideal apparatus state.

That is, while the sensitivity predicting unit 803 comparing the actual measurement result and the ideal value and estimating and predicting a current apparatus is present in the first embodiment, such estimation is not performed in the present embodiment.

Figure 17:
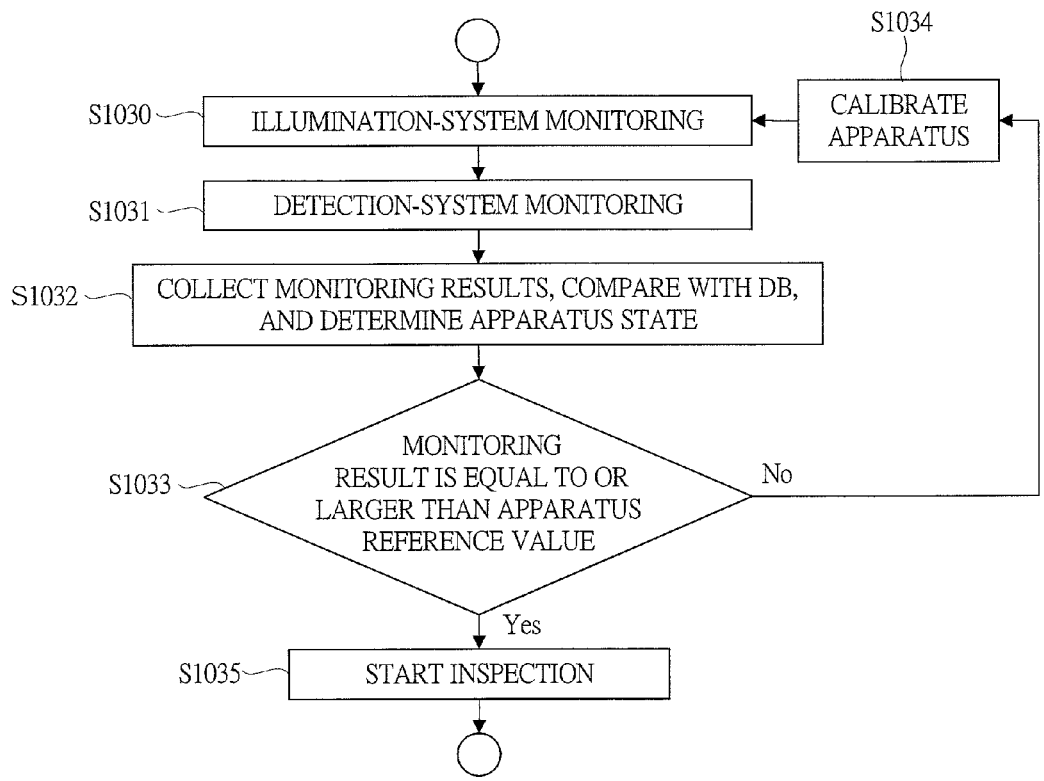
FIG. 17 is a flowchart of a monitoring and calibrating process procedure by a control unit according to the second embodiment of the present invention.

FIG. 17 is a flowchart of a monitoring and calibrating process procedure by this control unit 800-2.

First, the illumination-system monitoring unit 150 performs monitoring of the illumination system (step S1030). Also, the detection-system monitoring unit 250 performs monitoring of the state of the detection system (step S1031). The monitoring results at step S1030 and step S1031 are sent to the comparing unit 802. The comparing unit 802 makes a comparison with the database 805 to determine a current apparatus state of the dark-field defect inspecting apparatus (step S1032). The comparing unit 802 compares the apparatus state by making a comparison with the database 805 and an apparatus reference arbitrarily set (step S1033).

When the state is equal to or smaller than the reference, adjustment of the optical system is performed (step S1034), and then the procedure returns to monitoring of the illumination system (step S1030). Here, a portion to be calibrated is determined in advance through theoretical calculation or an optical-system simulation. Here, in an optical simulator, the portion to be calibrated may be determined by modeling the inspection subject, deriving an intensity of scattered light and others occurring from the inspection subject depending on the condition of the illumination optical system, and using the result of calculation of an optical intensity detected by a sensor.

On the other hand, when it is equal to or larger than the reference, the dark-field defect inspecting apparatus is inspected by, for example, issuing a warning to the operator (step S1035).

(Third Embodiment)

Next, a third embodiment of the present invention will be described.

In the dark-field defect inspecting apparatus according to the present invention, the surface of the inspection subject 1 is illuminated with the illumination light 100 from a direction with an angle with respect to the normal direction of the inspection subject 1, and a desired beam is formed on the inspection subject 1. Light scattered or diffracted from a foreign substance, a defect, or a pattern on the inspection subject 1 with the beam is collected by the objective lens 20 from a direction (upward) perpendicular to the normal direction of the inspection subject 1.

When a pattern formed on the inspection subject 1 is in the form of a repeated shape, diffracted light occurring from the repeated pattern is collected at the exit pupil of the objective lens 20 at regular intervals, and is therefore light-shielded by the spatial filter 21 placed at the exit pupil. On the other hand, the scattered light or diffracted light from portions other than the repeated pattern passes through the spatial filter 21 to be guided to the imaging lens 22. Then, these scattered light and diffracted light are imaged on the sensor 23. The inspection subject 1 is placed on the XY stage 300. By scanning with this XY stage 300 in an X direction and a Y direction, two-dimensional images of scattered light from the inspection subject 1 are obtained. Here, a distance between the inspection subject and the objective lens is measured by the inspection-subject height measuring unit 401. The information obtained through measurement by the inspection-subject height measuring unit 401 is adjusted by the Z stage 400. Based on the two-dimensional images obtained by the sensor 23, it is determined at the signal processing unit 500 whether a foreign substance and a defect are present. Here, the images are classified by the signal processing unit 500 for each foreign substance type or each defect type, where the size is found, and the result is then displayed on the monitor 501.

The illumination light 100 is generated by the "illumination system" formed of the laser 101, the beam expander 102, the attenuator 103, the polarization control element 104, the mirrors 105A and 105B, and the lens 106, which is same the first embodiment. Also, the illumination-system monitoring unit 150 for monitoring the intensity and polarization state of the illumination light 100, the detection-system monitoring unit 250, and a control unit 800-3 controlling the chip for monitoring 60 that generates a detection-system light source for monitoring are provided, which is also same as the first embodiment.

Figure 18:
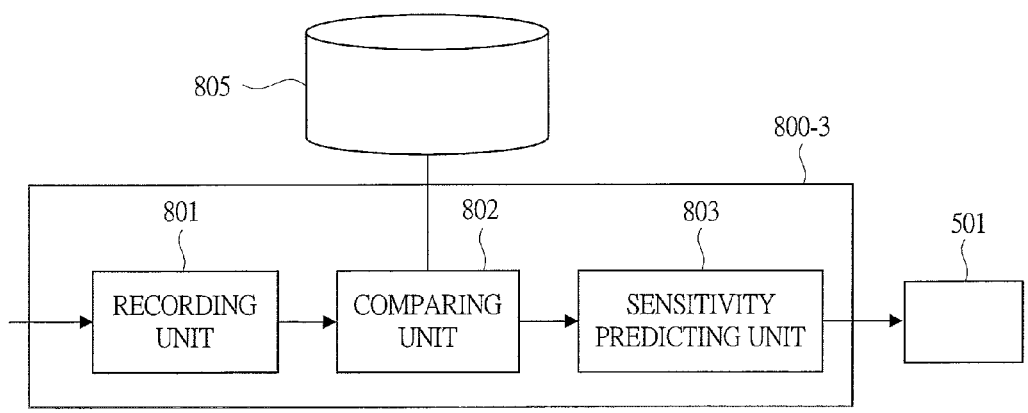
FIG. 18 is a block diagram of an inner structure of a control unit according to a third embodiment of the present invention.

FIG. 18 is a block diagram of an inner structure of a control unit 800-3 according to the third embodiment of the present invention. This control unit 800-3 is configured to include the recording unit 801, the comparing unit 802, and the sensitivity predicting unit 803.

The recording unit 801 is a circuit recording monitored data.

The comparing unit 802 is a circuit comparing the record data recorded in the recording unit 801 and the database 805 of ideal values.

The sensitivity predicting unit 803 is a circuit predicting an apparatus sensitivity from a difference between the recorded data and the ideal values.

The database 805 is a database of theoretical values created by calculating, in advance, characteristics of the light source and elements at the time of monitoring and using these to perform theoretical calculation and optical simulations. Here, in an optical simulator, the result obtained by modeling the inspection subject, deriving an intensity of scattered light and others occurring from the inspection subject depending on the condition of the illumination optical system, and calculating an optical intensity detected by a sensor may be used as a database.

That is, unlike the first embodiment and the second embodiment, in the present embodiment, the feedback control unit 804 is not present. In this manner, in an environment where automatic correction is not performed on the apparatus, a simple circuit structure can be achieved.

Figure 19:
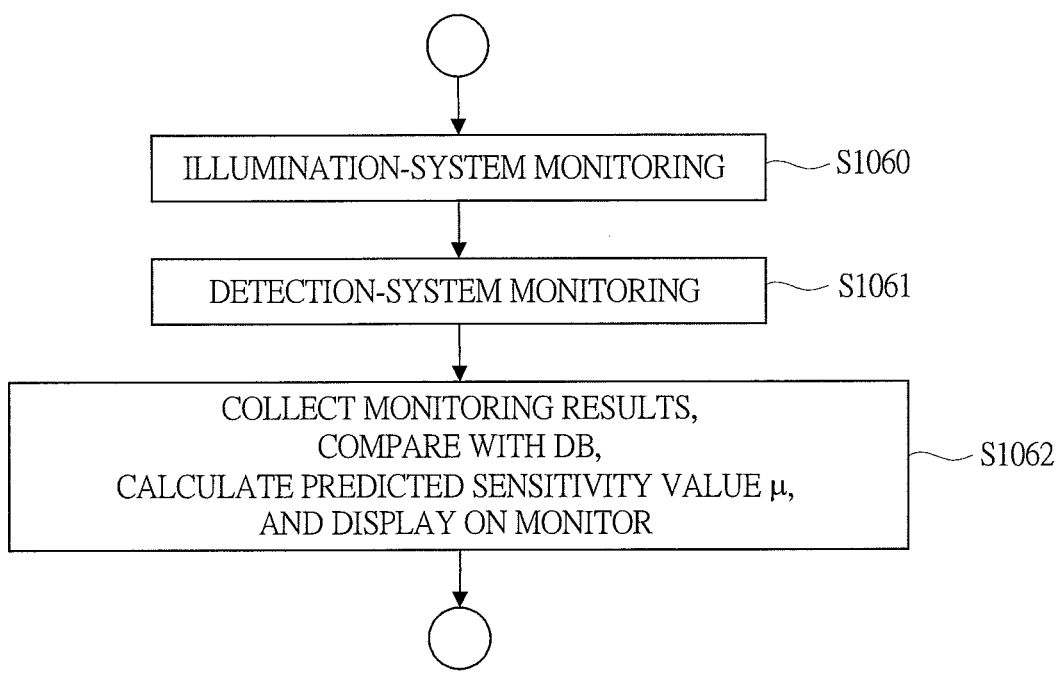
FIG. 19 is a flowchart of a monitoring process procedure by the control unit according to the third embodiment of the present invention.

FIG. 19 is a flowchart of a monitoring process procedure by the control unit 800-3 according to the third embodiment of the present invention.

First, the illumination-system monitoring unit 150 monitors the state of the illumination system (step S1060). Also, the detection-system monitoring unit measures the state of the detection system (step S1061). These detected values are transmitted to the comparing unit 802.

The comparing unit 802 collects these measurement results for comparison with the theoretical values of the database 805. Then, from a deviation occurring between the ideal values of the database 805 and the monitoring values, a detection sensitivity is predicted (step S1062).

Note that the monitoring process of the illumination-system monitoring unit 150 and the monitoring process of the detection-system monitoring unit 250 are same as those of the first embodiment, and therefore are omitted herein. See FIGS. 5 and 6, and their descriptions.

Next, apparatus sensitivity prediction using the apparatus state monitoring results is described. The inspection sensitivity of the inspection apparatus indicates a size of a foreign substance or defect detectable on a semiconductor wafer (inspection subject 1) or scattering light intensity itself from the foreign substance or defect. When the apparatus state is deviated from an ideal condition, the inspection sensitivity is decreased. Thus, an index indicating an inspection sensitivity is calculated from a difference between a physical quantity representing the apparatus state monitored and an ideal state of that physical quantity, and apparatus calibration is performed so that the inspection sensitivity is kept equal to or higher than a certain value.

Here, a physical quantity representing the apparatus state indicates an intensity distribution of the illumination system, a polarization state distribution, a detection-lens focal length, a sensor sensitivity, and others. Also, monitoring of each physical quantity is performed during measurement of the inspection subject 1 or always. Here, as an ideal value of the physical quantity to be monitored, all or any one of the following is used: a design value, a value obtained through theoretical calculation, and a value calculated from an optical simulation. Also, in addition to parameters for illumination system, the detection system, and others, parameters of temperature, atmospheric pressure, and moisture, which are parameters representing the environment inside the apparatus, are also monitored at the same time. In general, the characteristics of an optical element fluctuate depending on the usage environment. For example, a refractive index of glass forming a lens has temperature dependency, and the focal length, wave aberration, and others fluctuate depending on the temperature near the lens. Therefore, in adjustment of the optical element, the parameters regarding the apparatus environment described above are required to be taken into consideration.

Figure 20:
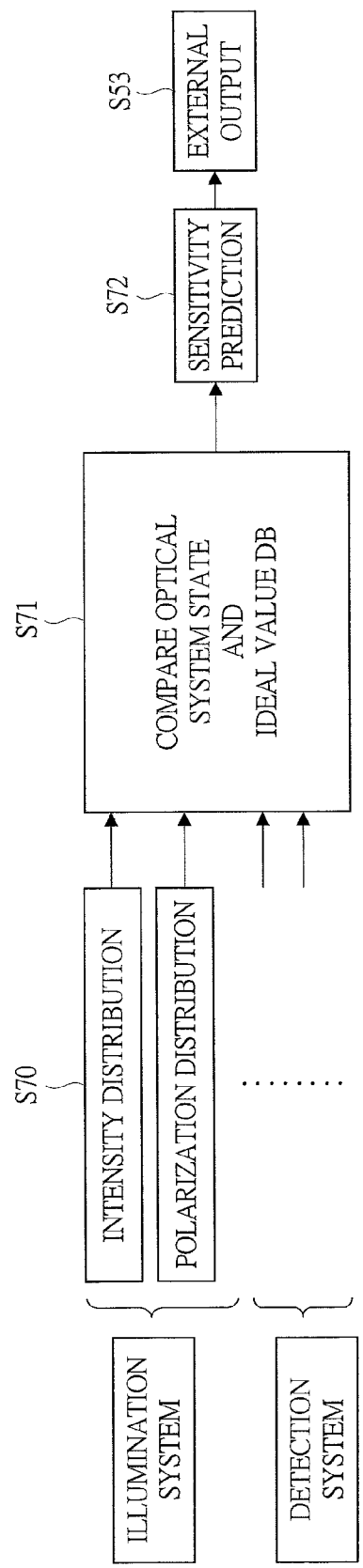
FIG. 20 is a flowchart of an apparatus calibrating process procedure.

FIG. 20 is a flowchart of an apparatus calibrating process procedure. With reference to this drawing, the apparatus calibrating process procedure will be described.

First, the physical quantities of the illumination system and the detection system are received from the illumination-system monitoring unit 150 and the detection-system monitoring unit 250, respectively (step S70). The actual detection value is defined as Fi.

With (Equation 1) obtained by squaring a difference between Fi and an ideal value Gi and weighting the result with Ai, comparison with each ideal value stored in the database 805 is made (step S71). A sensitivity is then predicted by taking (Equation 3) using (Equation 2) representing a deviation of every monitoring value from ideal as an index (step S72). This index is externally output via the monitor 501, thereby allowing the operator to regard this index as a guideline for visually determining an apparatus state (step S73).

(Fourth Embodiment)

Next, a fourth embodiment of the present invention will be described. Also in the present embodiment, a structure of a dark-field defect inspecting apparatus is same as that of FIG. 2.

The surface of the inspection subject 1 is illuminated with the illumination light 100 emitted from the laser 101 from a direction with an angle with respect to the normal direction of the inspection subject 1, and a desired beam is formed on the inspection subject 1. Light scattered or diffracted from a foreign substance, a defect, or a pattern on the inspection subject 1 with the beam is collected by the objective lens 20 from a direction (upward) perpendicular to the normal direction of the inspection subject 1. When a pattern formed on the inspection subject 1 is in the form of a repeated shape, diffracted light occurring from the repeated pattern is collected at the exit pupil of the objective lens 20 at regular intervals, and is therefore light-shielded by the spatial filter 21 placed at the exit pupil. On the other hand, the scattered light or diffracted light from portions other than the repeated pattern passes through the spatial filter 21 to be guided to the imaging lens 22, and is then imaged on the sensor 23.

The illumination light 100 is generated by the illumination system, which is similar to the first embodiment.

The inspection subject 1 is placed on the XY stage 300, and scanning is made with the XY stage 300 in an XY directions (a plane direction). With this, the sensor 23 can obtain a two-dimensional image of scattered light of the inspection subject 1.

A distance between the inspection subject 1 and the objective lens 20 is measured by the inspection-subject height measuring unit 401, and is adjusted by the Z stage 400. With this adjustment, an automatic focusing function can be achieved.

Based on the two-dimensional images obtained by the sensor 23, the signal processing unit 500 determines whether a foreign substance or a defect is present. The signal processing unit 500 makes a classification for each foreign substance and defect type to find the size, and displays the results on the monitor 501.

A control unit 800-4 controls the illumination-system monitoring unit 150, the detection-system monitoring unit 250, and the chip for monitoring 60 generating a light source for monitoring. Note that the structure and behaviors of the illumination-system monitoring unit 150 and the detection-system monitoring unit 250 and the structure of the chip for monitoring 60 are same as those in the first embodiment, and therefore are omitted herein.

Figure 21:
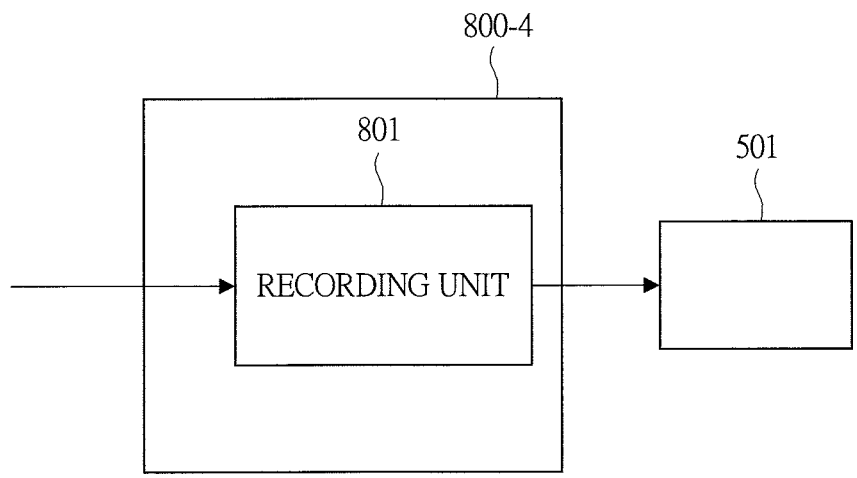
FIG. 21 is a block diagram of an inner structure of a control unit according to a fourth embodiment of the present invention.

FIG. 21 is a block diagram of an inner structure of the control unit 800-4 according to the present embodiment. In contrast to the first embodiment in which up to feedback is taken into consideration, in the present embodiment, the detection result of each monitoring unit is output only to the monitor 501. Therefore, in the control unit 800-4, only the recording unit 801 is included. The recording unit 801 is an output control circuit for outputting the detection results of each monitoring unit to the monitor 501. Note that, as required, an ideal value according to various conditions can be read from the database 805.

Figure 22:
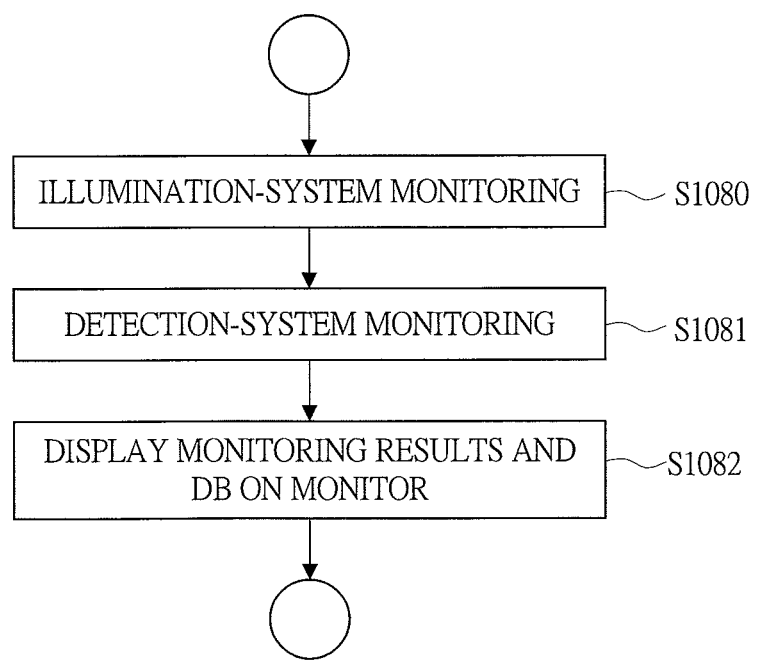
FIG. 22 is a flowchart of a monitoring process procedure in a dark-field defect inspecting apparatus according to the fourth embodiment of the present invention.

FIG. 22 is a flowchart of a monitoring process procedure in the dark-field defect inspecting apparatus according to the present embodiment. By using this, operation of the control unit 800-4 will be described.

First, the illumination-system monitoring unit 150 transmits the monitoring results to the recording unit 801 (step S1080). Also, the detection-system monitoring unit 250 transmits the monitoring results to the recording unit 801 (step S1081). The recording unit 801 reads an ideal value from the database 805 as required according to various conditions, and outputs the value together with the detection result of each monitoring unit to the monitor 501 (step S1082).

With the above structure, the monitored values can be disclosed from the monitor 501 to the operator of the dark-field defect inspecting apparatus. With this, the operator can check the apparatus state of the dark-field defect inspecting apparatus as appropriate. As a result, this can be a chance to adjust the dark-field defect inspecting apparatus.

(Fifth Embodiment)

A fifth embodiment will be described below with reference to the drawings. A difference between the first embodiment and the fifth embodiment is that details of a method of monitoring a wave aberration of a detection lens are described in the present embodiment.

The structure of the dark-field defect inspecting apparatus in the present embodiment is similar to that of the first embodiment illustrated in FIG. 2. Therefore, with reference to FIG. 2, the apparatus structure will be described.

The surface of the inspection subject 1 is illuminated with the illumination light 100 emitted from the laser 101 from a direction at an angle with respect to the normal direction to form a desired beam on the inspection subject 1.

Light scattered or diffracted from a foreign substance, a defect, or a pattern on the inspection subject 1 with the beam is collected by the objective lens 20 from a direction (in the drawing, upward) perpendicular to the normal direction of the inspection subject 1. When a pattern formed on the inspection subject 1 is in the form of a repeated shape, diffracted light occurring from the repeated pattern is collected at the exit pupil of the objective lens 20 at regular intervals, and is therefore light-shielded by the spatial filter 21 placed at the exit pupil.

On the other hand, the scattered light or diffracted light from portions other than the repeated pattern passes through the spatial filter 21 to be guided to the imaging lens 22, and is then imaged on the sensor 23. Also, at the position of the spatial filter 21, a detector is provided in the present embodiment, branching light by a half mirror not shown to observe a pupil surface.

The illumination light 100 is generated by the illumination system, which is same as the first embodiment.

The inspection subject 1 is placed on the XY stage 300. Also, the inspection subject 1 is scanned with the XY stage 300 in an XY direction (a plane direction). With this, the sensor 23 can obtain an imaging image of scattered light of the inspection subject 1.

A distance between the inspection subject 1 and the objective lens 20 is measured by the inspection-subject height measuring unit 401. From this measurement result, the distance between the inspection subject 1 and the objective lens 20 is adjusted by the Z stage 400. With this adjustment of the distance between the inspection subject 1 and the objective lens 20, an automatic focusing function can be achieved.

Based on the imaging images obtained by the sensor 23, the signal processing unit 500 determines whether a foreign substance or a defect is present. The signal processing unit 500 makes a classification for each foreign substance and defect type to find the size, and displays the results on the monitor 501.

Figure 23:
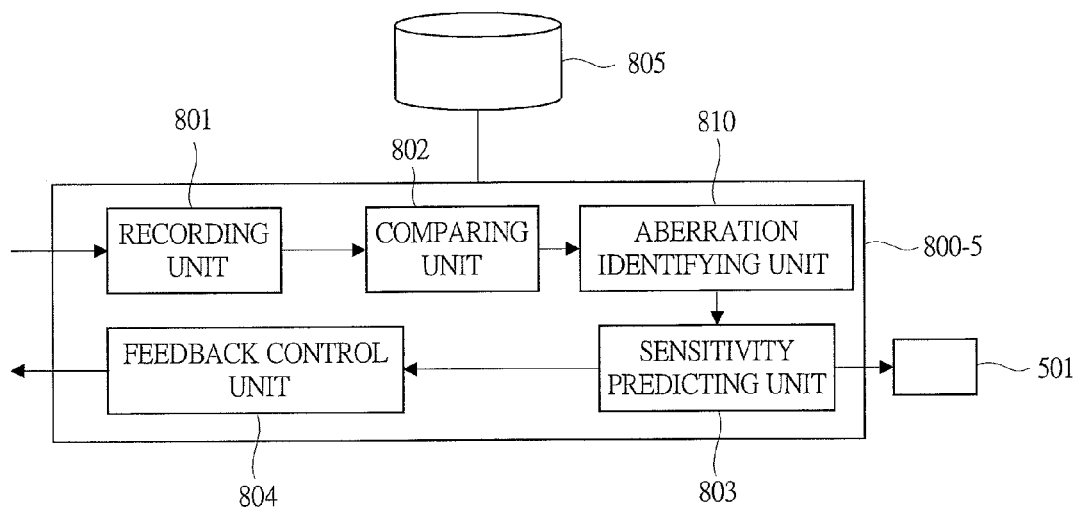
FIG. 23 is a block diagram representing an inner structure of a control unit 800-5 according to a fifth embodiment of the present invention.

Also in the present embodiment, a control unit 800-5 is a control circuit that compares the values obtained by the illumination-system monitoring unit 150 and the detection-system monitoring unit 250 with each other and performs feedback control. FIG. 23 is a block diagram representing an inner structure of the control unit 800-5 according to the present embodiment.

The control unit 800-5 according to the present embodiment is configured to include the recording unit 801, the comparing unit 802, an aberration identifying unit 810, the sensitivity predicting unit 803, and the feedback control unit 804.

The recording unit 801 is a circuit recording the monitored data of the illumination-system monitoring unit 150 and detection-system monitoring unit 250.

The comparing unit 802 is a circuit comparing the data recorded in the recording unit 801 with an ideal value in the database 805. Prior to processing at the comparing unit 802, monitoring values depending on the characteristics of a light source and elements at the time of monitoring are calculated in advance.

The aberration identifying unit 810 is a circuit to be used to identify a wave aberration of the detection lens.

The sensitivity predicting unit 803 is a circuit estimating and predicting a current apparatus sensitivity from a difference between the recorded data and the ideal values.

The feedback control unit 804 is a circuit performing feedback onto each operating unit of the apparatus according to a predicted sensitivity predicted by the sensitivity predicting unit 803.

The database 805 is a database of ideal values for use by the comparing unit 802. In this database 805, ideal values are input through theoretical calculation, optical simulations, and others. Parameters of the ideal values in this database 805 include information about an intensity distribution of the illumination optical system, a polarization state distribution, a focal length of the imaging lens 22, an image degraded due to wave aberrations of the objective lens and the imaging lens, sensitivity of the sensor 23, and others. With these as parameters, many theoretical calculations are performed in advance to create a database.

Schemes of illumination-system monitoring and detection-system monitoring will be described hereinafter. Here, a method of monitoring a wave aberration representing an imaging characteristic of a detection lens, which is different from the first embodiment, will be mainly described. Note that the structure of the optical system is same as that of FIG. 2.

With influences of the wave aberration of the detection lens formed of the objective lens 20 and the imaging lens 22, an image imaged on the sensor 23 is expanded.

Here, the wave aberration is represented by a spatial two-dimensional phase distribution on a pupil surface, and this phase distribution can be resolved by a Zernike polynominal. Each term of this Zernike polynominal represents a different aberration component, such as spherical aberration, coma aberration, or astigmatism aberration. A Zernike coefficient is a weighting coefficient representing the magnitude of each aberration component in this Zernike polynominal. In the present embodiment, an image obtained on the apparatus and a distribution function of an image depending on an aberration theoretically calculated with the Zernike coefficient representing a wave aberration as a parameter are compared with each other, thereby analyzing the Zernike coefficient representing the wave aberration of the detection lens.

As light for use at the time of this analysis of the Zernike coefficient, scattered light from the inspection target subject may be used, or diffracted light from a diffraction grating for use at the time of detection-system monitoring or a point source of light may be used. In any case, from a change of the image due to a wave aberration, the magnitude of the wave aberration is obtained through an inverse operation. Note that the descriptions below will be made regarding using a point image.

Figure 24:
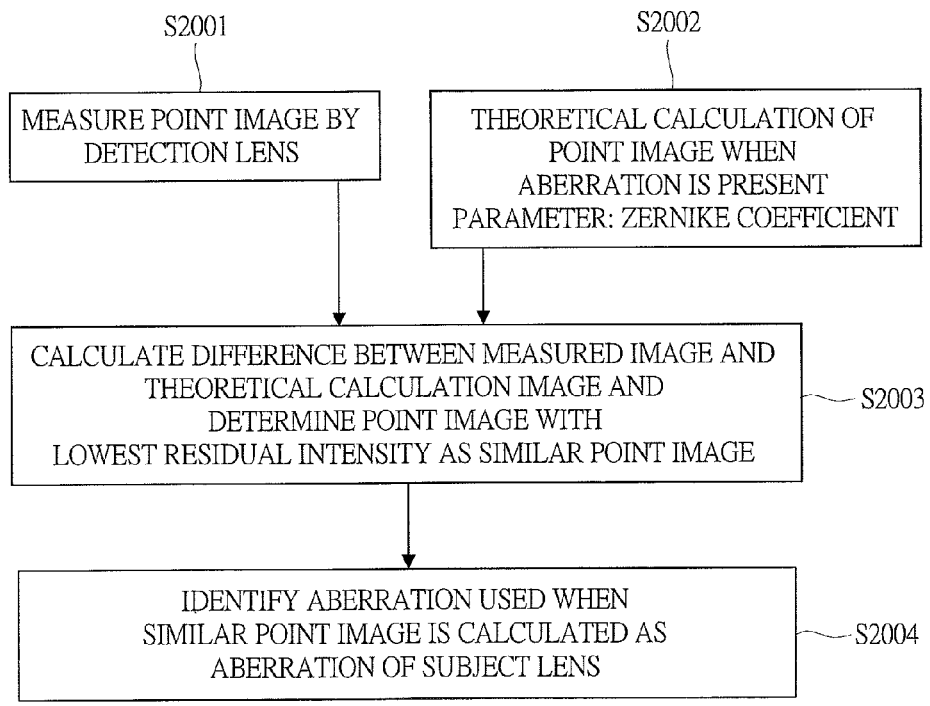
FIG. 24 is a flowchart of a procedure of identifying an aberration of a detection lens according to the fifth embodiment of the present invention.

FIG. 24 is a flowchart illustrating a procedure of identifying an aberration of a detection lens according to the present embodiment. With reference to this, a flow of identifying an aberration of the detection lens will be described.

Light emitted from a point source of light is introduced to the imaging lens 22, and is imaged on the sensor 23. The signal processing unit 500 records the imaged point image in a recording unit in the control unit 800-5 (step S2001). Also, with a Zernike coefficient representing a wave aberration being taken in advance as a parameter, point images with various wave aberrations of the detection lens are theoretically calculated, and are recorded in the database 805 (step S2002).

Next, by the comparing unit 802 in the control unit 800-5, a difference between the point image obtained at step S2001 and each of many point images calculated at step S2002 is calculated, and residual intensity is calculated at all or part of the images (step S2003). Then, in the aberration identifying unit 810 of the control unit 800-5, with taking a point image having the lowest residual intensity as a similar point image, an aberration when the similar point image is calculated is identified as an aberration of the imaging lens (step S2004).

Alternatively, instead of using a difference image, a search for a similar point image may be made by using a profile of an intensity distribution of each image about a plurality of axes in the image, with a difference as a reference.

Here, the point source of light collects light flux so that they are at a spot on a diffusion plate, thereby obtaining a point source of light from the diffusion plate for use. At this time, the diffusion plate for use preferably has a small angle of elevation of a scattered light amount and azimuth dependency on azimuth (ideally, zero). Note that although the use of the diffusion plate is described in the present embodiment, a microsphere having a diameter smaller than the wavelength may be used in place of the diffusion plate and be irradiated with illumination light for obtainment. Also, a point source of light itself may be placed at an end of the XY stage 300.

Note that monitoring of the illumination system and detection system other than aberration and feedback of the results to the apparatus are same as those in the first embodiment, and therefore are not described herein.

As described above, it is possible to provide means for quickly performing automatic calibration of the imaging lens 22 through monitoring by extracting data of an approximate wave aberration from the database according to the present embodiment.

(Sixth Embodiment)

A sixth embodiment is described below by using the drawing.

A preferred aim of the present embodiment is to provide more accurate automatic calibrating means by modifying a part of the process flow of the fifth embodiment.

Figure 25:
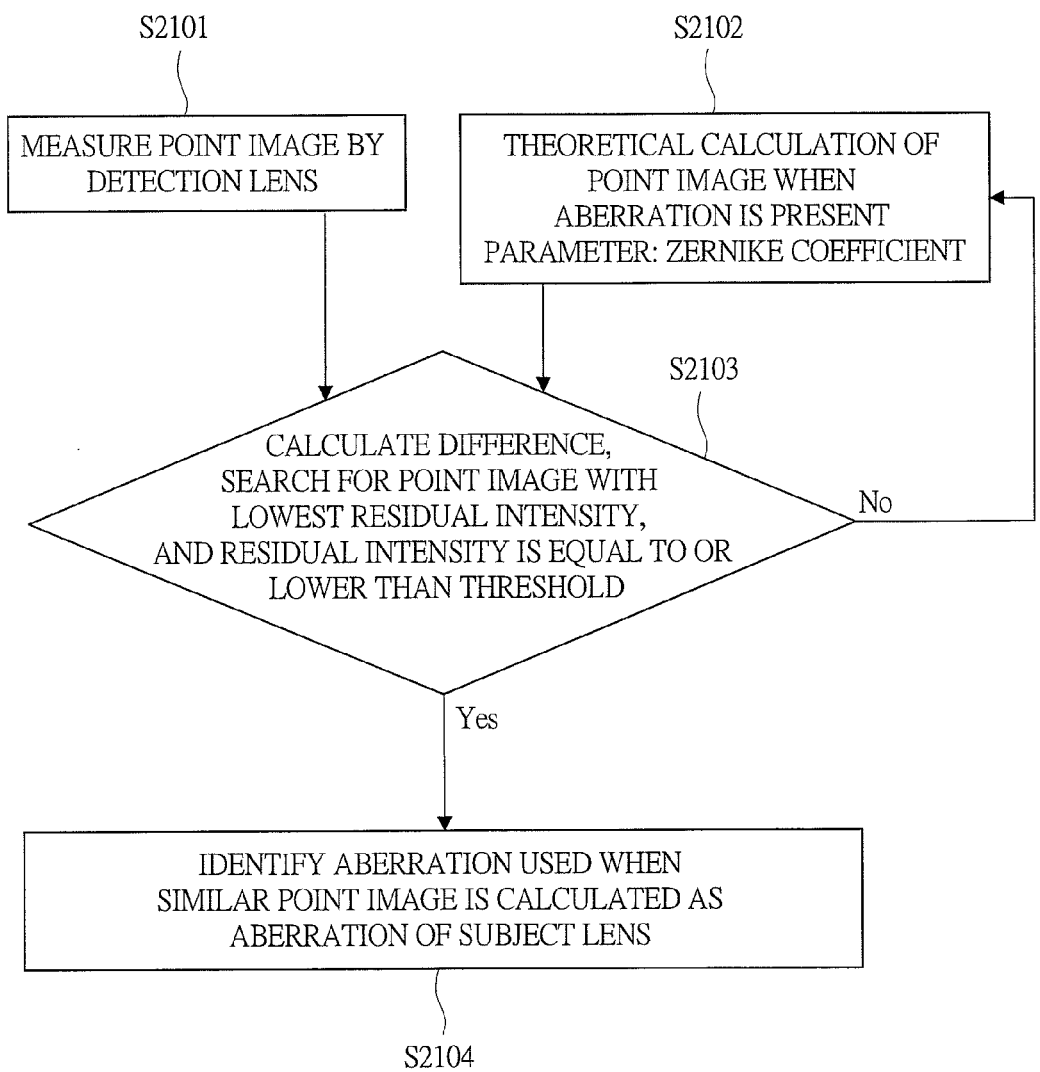
FIG. 25 is a flowchart of a procedure of identifying an aberration of a detection lens according to a sixth embodiment of the present invention.

FIG. 25 is a flowchart of a procedure of identifying an aberration of a detection lens according to the present embodiment. With reference to this, a flow of identifying an aberration of the detection lens according to the sixth embodiment will be described. Note that the case of using a point image will be described also in the present embodiment.

Light emitted from a point source of light is introduced to the imaging lens 22, and is imaged on the sensor 23. The signal processing unit 500 records the imaged point image in a recording unit in the control unit 800-5 (step S2101). Also, with a Zernike coefficient representing a wave aberration being taken in advance as a parameter, point images with various wave aberrations of the detection lens are theoretically calculated, and are recorded in the database 805 (step S2102).

Next, by the comparing unit 802 in the control unit 800-5, a difference between the point image obtained at step S2101 and each of many point images calculated at step S2102 is calculated. Then, the comparing unit 802 calculates a residual intensity at all or part of the difference images, and compares a minimum value of the residual intensity and an arbitrarily-determined threshold (step S2103).

At this time, when the minimum residual intensity is equal to or larger than the threshold (step S2103: No), theoretical calculations are performed on many point images with an aberration parameter being changed until the minimum residual intensity is equal to or smaller than the threshold, thereby searching for a similar point image.

On the other hand, when the minimum residual intensity is equal to or smaller than the threshold (step S2103: Yes), a point image with the lowest residual intensity of the difference image is taken as a similar point image (step S2104). An aberration upon calculating this similar point image is identified as an aberration of the imaging lens, thereby completing automatic calibration of the imaging lens 22.

As described above, it is possible to provide means for quickly and highly accurately performing automatic calibration of the imaging lens 22 through monitoring by extracting data of an approximate wave aberration from the database according to the present embodiment.

Note that not only a point image but also scattered light from the inspection subject may be used for aberration identification, and diffracted light from the diffraction grating for use at the time of detector monitoring may be used.

Alternatively, in place of using a difference image, a search for a similar point image may be made by using a profile of an intensity distribution of each image on a plurality of axes in the image, with a difference as a reference.

(Seventh Embodiment)

A seventh embodiment will be described hereinafter with reference to the drawing.

A difference between the present (seventh) embodiment and the sixth embodiment resides only in a flow of identifying an aberration of the imaging lens 22, and therefore other descriptions will be omitted herein.

Figure 26:
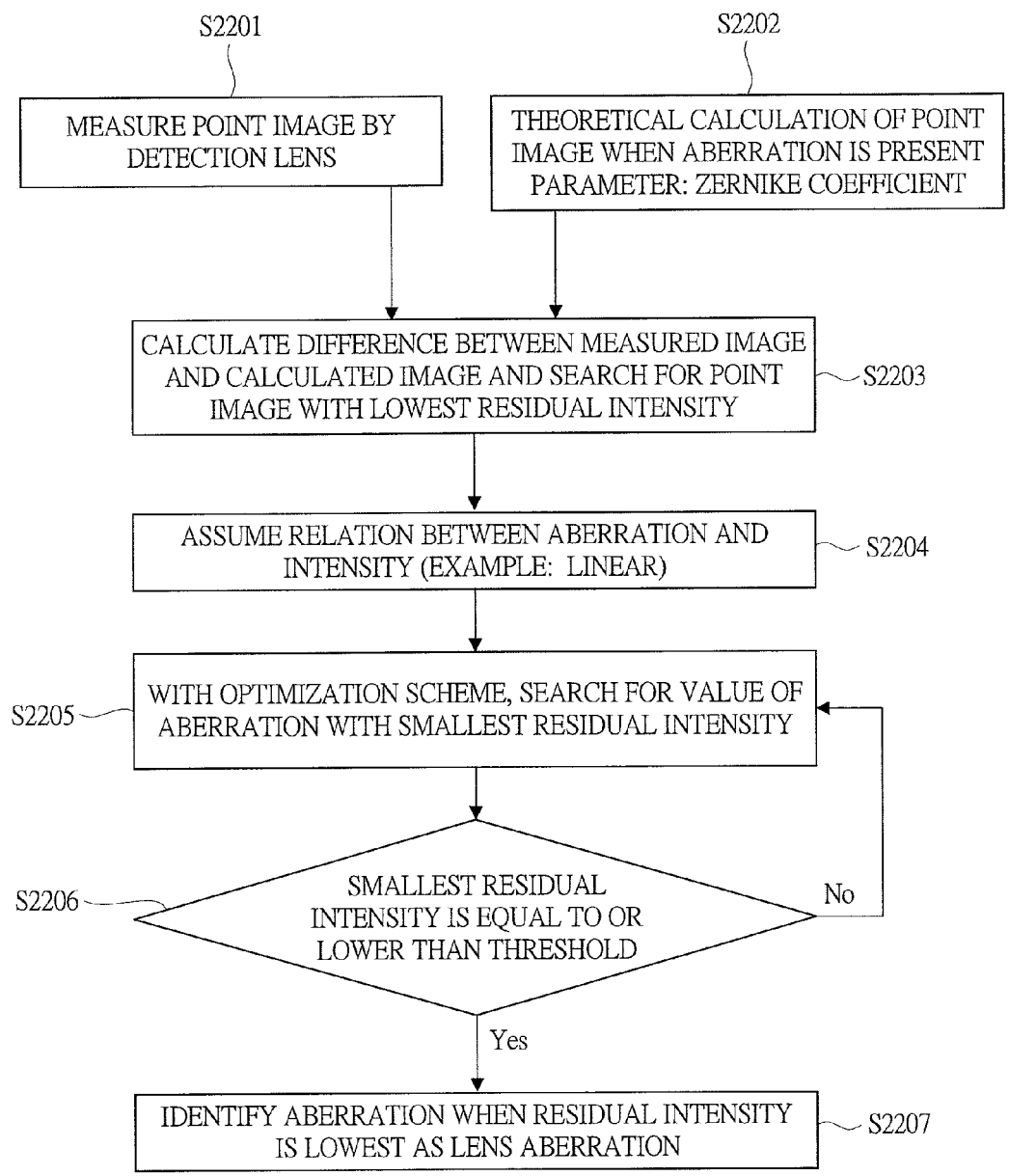
FIG. 26 is a flowchart of a procedure of identifying an aberration of a detection lens according to a seventh embodiment of the present invention.

FIG. 26 is a flowchart illustrating a procedure of identifying an aberration of the detection lens according to the present embodiment. With reference to this, the flow of identifying an aberration of the detection lens according to the seventh embodiment will be described.

Light emitted from a point source of light is introduced to a detection lens, and is imaged on the sensor 23. Image data found from this imaged point image is recorded in the recording unit in the control unit 800-5 (step S2201).

Also, with a Zernike coefficient representing an aberration being taken in advance as a parameter, point images with various wave aberrations of the detection lens are theoretically calculated. Then, the calculation results are recorded on the database 805 (step S2202).

Next, by the comparing unit 802 in the control unit 800-5, a difference between each piece of image data of the point images obtained at step S2201 and each of the calculation results of many point images stored in the database 805 at step S2202 is found. Then, a residual intensity is calculated at all or part of the difference images, and an image having a minimum value of the residual intensity is selected. Here, when the change of the aberration is small, the change of the intensity distribution of the point images can be approximated to a change onto the aberration (step S2204).

The change of the intensity modulation found at this step S2204 is made as a linear change or a non-linear change, and an equation is assumed. By using an optimizing method within a scope in which this assumption holds, a search is made for an aberration parameter with the minimum residual intensity (step S2205). As an optimizing method, it can be considered to use Levenberg-Marquardt Method or a steepest descent method, but the method is not restricted to these.

The minimum value of the residual intensity found and an arbitrarily set threshold are compared with each other (step S2206) and, when this minimum value is equal to or smaller than the threshold (step S2206: Yes), a point image having the lowest residual intensity of the difference image is assumed to be a similar point image. And an aberration of this point image assumed as a similar point image is identified as an aberration of the imaging lens (step S2207).

On the other hand, when the minimum value found at step S2206 is equal to or larger than the threshold (step S2206: No), it is highly possible that the value is a local minimum (a local minimum value). Therefore, constrains due to correlation between aberration parameters in the optimizing method are reconsidered, and then optimization is performed again.

At this time, instead of using a difference image, a search for a similar point image may be made by using a profile of an intensity distribution of each image about a plurality of axes in the image, with taking a difference as a reference.

Furthermore, as with the fifth embodiment, not only a point image but also scattered light from the inspection subject may be used for aberration identification, and diffracted light from the diffraction grating for use at the time of detector monitoring may be used.

While the invention made by the inventors has been specifically described in the foregoing based on the embodiments, it is needless to say that the present invention is not restricted by the embodiments described above, and can be variously modified within a scope of not deviating from the gist of the invention.

Industrial Applicability

While the present invention has been described as being assumed to be applied in a dark-field defect inspecting apparatus in semiconductor manufacturing and magnetic head manufacturing, the intended purposes are not necessarily restricted to the above, and the present invention can also be applied to technological fields, such as inspection of microbes and others that cannot be observed with an electron microscope.

Description of Reference Numerals
- 20 .... Objective lens, 21 .... Spatial filter, 22 .... Imaging lens, 23 .... Sensor,
- 24 .... Half mirror, 60 .... Chip for monitoring,
- 100 .... Illumination light, 101 .... Laser, 102 .... Beam expander
- 103 .... Attenuator, 104 .... Polarization control element, 105A, 105B .... Mirror,
- 106 .... Lens, 150 .... Illumination-system monitoring unit,
- 250 .... Detection-system monitoring unit, 251 .... Sensor, 300 ... XY stage,
- 400 ... Z stage, 401 .... Inspection-subject height measuring unit,
- 500 .... Signal processing unit, 501 .... Monitor,
- 800, 802-2, 800-3, 800-4 .... Control unit, 801 .... Recording unit,
- 802 .... Comparing unit, 803 .... Sensitivity predicting unit,
- 804 .... Feedback control unit, 805 .... Database

The invention claimed is:

1. A dark-field defect inspecting method of obtaining, by a first sensor of a detection system, a signal of scattered light occurring due to illumination light illuminating a surface of an inspection subject, from the surface of the inspection subject and detecting a foreign substance or a defect on the inspection subject based on the signal obtained by the first sensor, the method comprising:
   an illumination light monitoring step of measuring either one or both of an intensity distribution and a polarization state distribution of the illumination light;
   a detection system monitoring step of detecting an imaging characteristic of a detection lens and a state of operation of a stage on which the inspection subject is placed, by detecting light input to the detection system by a second sensor; and
   a feedback control step of comparing detection results in the illumination light monitoring step and the detection system monitoring step and predetermined values and adjusting either one or both of the illumination light and the detection system so that differences between the detection results and the predetermined values are each equal to or smaller than an allowable value.

2. The dark-field defect inspecting method according to claim 1, wherein the illumination light monitoring step measures either one or both of the intensity distribution and the polarization state distribution of the illumination light by using a specular reflected light.

3. The dark-field defect inspecting method according to claim 1, wherein the illumination light monitoring step measures either one or both of the intensity distribution and the polarization state distribution of the illumination light on the stage serving as an inspection surface for the inspection subject.

4. The dark-field defect inspecting method according to claim 1, wherein the illumination light is generated by an illumination system having a laser as a light source, and,
   in the illumination light monitoring step, from measurement results of light beams in a process of generating the illumination light, either one or both of the intensity distribution and the polarization state distribution of the illumination light on an inspection surface are estimated.

5. The dark-field defect inspecting method according to claim 1, wherein the detection system monitoring step detects, by the second sensor, the scattered light obtained by obliquely illuminating a reflective-type optical element with spot light, the optical element having a known characteristic and being placed on the stage serving as an inspection surface for the inspection subject.

6. The dark-field defect inspecting method according to claim 1, wherein the detection system monitoring step detects, by the second sensor, predetermined light obtained by using a point source of light placed on the stage serving as an inspection surface for the inspection subject and a transmission-type optical element having a known characteristic.

7. The dark-field defect inspecting method according to claim 1, further comprising an apparatus anomaly checking step of recording changes with time of the detection results in the illumination light monitoring step and the detection system monitoring step and determining an anomaly of an apparatus configuration through a statistical process.

8. The dark-field defect inspecting method according to claim 1, further comprising a detection result output step of simultaneously displaying the detection results in the illumination light monitoring step and the detection system monitoring step and the ideal values.

9. A dark-field defect inspecting method of obtaining, by a first sensor of a detection system, a signal of scattered light occurring due to illumination light illuminating a surface of an inspection subject, from the surface of the inspection subject and detecting a foreign substance or a defect on the inspection subject based on the signal obtained by the first sensor, the method comprising:
   an illumination light monitoring step of measuring either one or both of an intensity distribution and a polarization state distribution of the illumination light;
   a detection system monitoring step of detecting an imaging characteristic of a detection lens and a state of operation of a stage on which the inspection subject is placed, by the scattered light input to the detection system by a second sensor;
   an environment measuring step of measuring either one or both of temperature and an atmospheric pressure upon execution of the illumination light monitoring step and the detection system monitoring step; and
   a feedback control step of comparing detection results in the illumination light monitoring step, the detection system monitoring step, and the environment measuring step and predetermined values and adjusting either one or both of the illumination light and the detection system so that differences between the detection results and the predetermined values are each equal to or smaller than an allowable value.

10. The dark-field defect inspecting method according to claim 9, further comprising a detection result output step of displaying the detection results in the illumination light monitoring step and the detection system monitoring step and the ideal values.

11. A dark-field defect inspecting apparatus comprising: an illumination system outputting illumination light; a detection system detecting scattered light of the illumination light with which an inspection subject is illuminated; and a control unit, the apparatus obtaining, by a first sensor of the detection system, a signal of the scattered light occurring due to the illumination light illuminating a surface of the inspection subject, from the surface of the inspection subject and detecting a foreign substance or a defect on the inspection subject based on the obtained signal, the illumination system including illumination light monitoring unit for measuring either one or both of an intensity distribution and a polarization state distribution of the illumination light, the detection system including detection system monitoring unit for detecting an imaging characteristic of a detection lens and a state of operation of a stage on which the inspection subject is placed, by detecting light input to the detection system by a second sensor, and the control unit comparing detection results of the illumination light monitoring unit and the detection system monitoring unit and predetermined values and adjusting either one or both of the illumination light and the detection system so that differences between the detection results and the predetermined values are each equal to or smaller than an allowable value.

12. The dark-field defect inspecting apparatus according to claim 11, wherein the illumination light monitoring unit measures either one or both of the intensity distribution and the polarization state distribution of the illumination light by using specular reflection light.

13. The dark-field defect inspecting apparatus according to claim 11, wherein the illumination light monitoring unit measures either one or both of the intensity distribution and the polarization state distribution of the illumination light on the stage serving as an inspection surface for the inspection subject.

14. The dark-field defect inspecting apparatus according to claim 11, wherein a light source of the illumination light is a laser inside the illumination system, and the illumination light monitoring unit estimates, from measurement results of light beams in a process of generating the illumination light, either one or both of the intensity distribution and the polarization state distribution of the illumination light on an inspection surface.

15. The dark-field defect inspecting apparatus according to claim 11, wherein the detection system monitoring unit detects, by the second sensor, the scattered light obtained by obliquely illuminating a reflective-type optical element with spot light, the optical element having a known characteristic and being placed on the stage serving as an inspection surface for the inspection subject.

16. The dark-field defect inspecting apparatus according to claim 11, wherein the detection system monitoring unit detects, by the second sensor, predetermined light obtained by using a point source of light placed on the stage serving as an inspection surface for the inspection subject and a transmission-type optical element having a known characteristic.

17. The dark-field defect inspecting apparatus according to claim 11, further comprising apparatus anomaly checking unit for recording changes with time of the detection results of the illumination light monitoring unit and the detection system monitoring unit and determining an anomaly of an apparatus configuration through a statistical process.

18. The dark-field defect inspecting apparatus according to claim 11, further comprising detection result output unit for simultaneously displaying the detection results of the illumination light monitoring unit and the detection system monitoring unit and the ideal values.

\* \* \* \* \*